US005612358A

United States Patent [19]

Ishimitsu et al.

[11] Patent Number: 5,612,358

[45] **Date of Patent: *Mar. 18, 1997**

[54] PYRIDINE COMPOUDS WHICH HAVE USEFUL INSECTICIDAL ACTIVITY

[75] Inventors: Keiichi Ishimitsu, Kanagawa; Haruhito Ohishi, Saitama; Renpei Hatano; Jun Mitsui, both of Kanagawa; Junji Suzuki, Toyama; Tomio Yamada; Nobuo Takakusa, both of Kanagawa, all of Japan

[73] Assignee: Nippon Soda Co., Ltd., Tokyo, Japan

[ * ] Notice: The term of this patent shall not extend beyond the expiration date of Pat. No. 5,304,566.

[21] Appl. No.: 117,470

[22] Filed: Sep. 7, 1993

Related U.S. Application Data

[63] Continuation of Ser. No. 700,165, Jul. 9, 1991, Pat. No. 5,304,566.

[30] Foreign Application Priority Data

| | | | |
|---|---|---|---|
| Oct. 6, 1989 | [JP] | Japan | 2-259966 |
| Dec. 27, 1989 | [JP] | Japan | 2-336231 |
| Mar. 9, 1990 | [JP] | Japan | 3-56611 |
| May 2, 1990 | [JP] | Japan | 3-115246 |
| Jul. 26, 1990 | [JP] | Japan | 2-196258 |

[51] Int. Cl.[6] ........................ C07D 213/36; A01N 43/36

[52] U.S. Cl. ........................ 514/357; 546/286; 546/300; 546/311; 546/329; 546/332; 546/334; 546/338; 514/344; 514/345; 514/352

[58] Field of Search .................................... 546/286, 300, 546/311, 329, 332, 334, 338; 514/344, 345, 352, 357

[56] References Cited

PUBLICATIONS

Hackh's Chemical Dictionary, p. 62, 1969.

Del Corona et al, *Boll. Chim. Farm,* vol. 118 (11), pp. 661–666 (1979).

Chemical Abstracts, vol. 115(9), Abstract No. 92,085a, p. 745, Sep. 2, 1991.

*Primary Examiner*—Zinna Northington Davis

*Attorney, Agent, or Firm*—Joseph C. Mason, Jr.; Louise A. Foutch

[57] ABSTRACT

An insecticidal compound of the formula

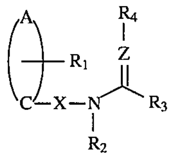

wherein

A completes a 5 or 6 membered aromatic ring selected from the group pyridyl, pyridyl substituted with $C_{1-5}$alkyl, $C_{1-5}$haloalkyl, $C_{1-5}$alkoxy, $C_{1-5}$alkylthio, $C_{1-5}$alkylsulfonyl, cyano, halogen, phenoxy or $C_{1-5}$dialkylamino, pyrazinyl, pyrazinyl substituted with $C_{1-5}$alkyl or halogen, pyrazolyl substitited with $C_{1-5}$alkyl, pyridazyl substituted with halogen, or thiazolyl substituted with halogen or $C_{1-5}$alkyl;

$R_1$ is hydrogen or $C_{1-5}$alkyl, $C_{1-5}$haloalkyl, $C_{1-5}$alkoxy, $C_{1-5}$alkylthio, $C_{1-5}$alkylsulfonyl, cyano, halogen, phenoxy, or $C_{1-5}$dialkylamino;

X is substituted or unsubstituted $C_{1-3}$alkylene or $C_{1-3}$alkylidene;

$R_2$ is hydrogen, monoalkylcarbamoyl, $C_{1-5}$dialkylcarbamoyl, $C_{1-5}$alkoyl, $C_{1-5}$alkyl substituted with halogen, $C_{1-5}$alkoxy, $C_{1-5}$alkylthio, $C_{1-5}$alkoxycarbonyl, cyano, aryl, haloaryl, $C_{1-5}$alkoxyaryl, furyl, thienyl, pyridyl, halopyridyl, thiazolyl or halothiazolyl, $C_{2-5}$alkyenyl, $C_{2-5}$alkynyl, $C_{3-6}$cycloalkyl, aryl, or the radical $-Y-R_5$ and an insecticidal acceptable salt thereof.

7 Claims, No Drawings

PYRIDINE COMPOUDS WHICH HAVE USEFUL INSECTICIDAL ACTIVITY

This is a continuation of application Ser. No. 07/700,165 filed on Jul. 9, 1991 now U.S. Pat. No. 5,304,566.

DESCRIPTION OF RELATED ART

The present invention relates to new amine derivatives, the processes for the production thereof and insecticides containing the said derivatives as effective compounds.

BACKGROUND ART

A large number of chemicals, for example, organophosphorus compounds such as parathion and malathion and carbamate compounds such as carbaryl and methomyl, have been developed and put to practical use as insecticides over many years. These insecticides have played a very great role for the improvement of agricultural production. However, in recent years some of these insecticides are regulated on their use because of problems such as environmental pollution due to residue or accumulation, or cause infestation of resistant insect pests as a result of long-term use. Therefore, there is a need to develop new chemicals which have excellent insecticidal characteristics over various types of insect pests including these resistant insect pests and which can be used safely.

The following compound is known as the isomer compound of this invention, which has no insecticidal activity.

TABLE 1
Structure Formula
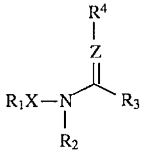
| Compound No. | $R_1X$ | $R_2$ | $R_3$ | Z | $R_4$ | Physical Properties [ ] m.p. °C. |
|---|---|---|---|---|---|---|
| 1 | 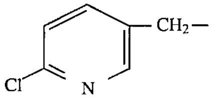 | H | H | N | CN | [123–126] |
| 2 | " | " | $CH_3$ | " | " | [141–143] |
| 3 | " | " | $CH_2Cl$ | " | " | [124–126] |
| 4 | " | " | $CH_2F$ | " | " | [151–152] |
| 5 | " | " | $CF_3$ | " | " | [112–114] |
| 6 | " | " | $C_2H_5$ | " | " | [120–122] |
| 7 | " | " | $C_3H_7(n)$ | " | " | [100–101] |
| 8 | " | " | 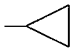 | " | " | [193.5–195] |
| 9 | " | " | $C_4H_9(t)$ | " | " | |
| 10 | " | " | $CH_2OCH_3$ | " | " | [128–128.5] |
| 11 | " | " | $CH_2SCH_3$ | " | " | [116–118] |
| 12 | 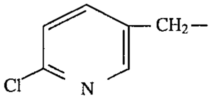 | " | $CH_2COOC_2H_5$ | N | CN | $n_D^{25.5}$ 1.5608 |
| 13 | " | " | $CH_2CH_2COOC_2H_5$ | " | " | |
| 14 | " | " | $CH_2NHCH_3$ | " | " | |
| 15 | " | " | $CH_2N(CH_3)_2$ | " | " | |
| 16 | " | " | $CH_2CH_2CH_2Cl$ | " | " | [114–115] |
| 17 | " | " | 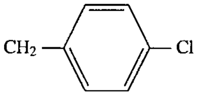 | " | " | [190–191] |
| 18 | " | " | $CH_2CN$ | " | " | [106–108] |
| 19 | " | " | $CH_2CH_2CN$ | " | " | |

TABLE 1-continued

Structure Formula

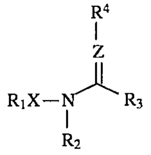

| Compound No. | $R_1X$ | $R_2$ | $R_3$ | Z | $R_4$ | Physical Properties [ ] m.p. °C. |
|---|---|---|---|---|---|---|
| 20 | " | " | 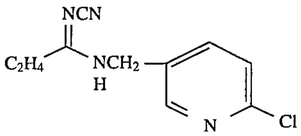 | " | " | [187–189] |
| 21 | " | $CH_3$ | H | " | " | $n_D^{25}$ 1.5918 |
| 22 | " | " | $CH_3$ | " | " | [101–103] |
| 23 | " | " | " | " | " | [161–162] HCl salt |
| 24 | " | " | $CH_2Cl$ | " | " | $n_D^{26.5}$ 1.5921 |
| 25 | " | " | $CH_2F$ | " | " | [79–80] |
| 26 | " | " | $CF_3$ | " | " | *1 |
| 27 | 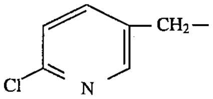 | $CH_3$ | $C_2H_5$ | N | CN | $n_D^{27}$ 1.5742 |
| 28 | " | " | $C_3H_7$(n) | " | " | [97–100] |
| 29 | " | " | 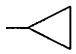 | " | " | $n_D^{24.5}$ 1.5829 |
| 30 | " | " | $C_4H_9$(t) | " | " | |
| 31 | " | " | $CH_2OCH_3$ | " | " | $n_D^{24}$ 1.5803 |
| 32 | " | " | $CH_2SCH_3$ | " | " | $n_D^{24.5}$ 1.6070 |
| 33 | " | " | $CH_2COOC_2H_5$ | " | " | $n_D^{25.5}$ 1.5604 |
| 34 | " | " | $CH_2CH_2COOC_2H_5$ | " | " | $n_D^{24.5}$ 1.5605 |
| 35 | " | " | $CH_2NHCH_3$ | " | " | $n_D^{25}$ 1.5861 |
| 36 | " | " | $CH_2N(CH_3)_2$ | " | " | $n_D^{25}$ 1.5577 |
| 37 | " | " | $CH_2CH_2Cl$ | " | " | |
| 38 | " | " | $CH_2CH_2CH_2Cl$ | " | " | $n_D^{25.5}$ 1.5830 |
| 39 | " | " | 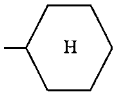 | " | " | |

TABLE 1-continued
Structure Formula
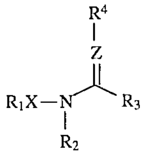
| Compound No. | $R_1X$ | $R_2$ | $R_3$ | Z | $R_4$ | Physical Properties [ ] m.p. °C. |
|---|---|---|---|---|---|---|
| 40 | " | " | 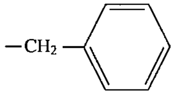 | " | " | |
| 41 | " | " | 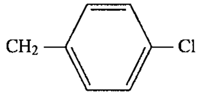 | " | " | $n_D^{25.5}$ 1.6040 |
| 42 | 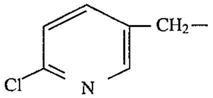 | $CH_3$ | $CH=CH_2$ | N | CN | |
| 43 | " | " | $CH_2CN$ | " | " | $n_D^{25}$ 1.5913 |
| 44 | " | " | $CH_2CH_2CN$ | " | " | [112–114] |
| 45 | " | " | 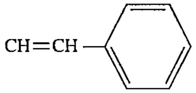 | " | " | |
| 46 | " | " | 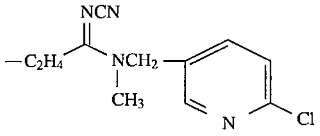 | " | " | [224–226] |
| 47 | " | $CHF_2$ | H | " | " | |
| 48 | " | " | $CH_3$ | " | " | $n_D^{24.5}$ 1.5423 |
| 49 | " | " | $C_2H_5$ | " | " | |
| 50 | " | $C_2H_5$ | H | " | " | [101–103] |
| 51 | " | " | $CH_3$ | " | " | [100–101] |
| 52 | " | " | $C_2H_5$ | " | " | |
| 53 | " | $C_3H_7(i)$ | H | " | " | [205–207] |
| 54 | " | " | $CH_3$ | " | " | |
| 55 | " | " | $C_2H_5$ | " | " | |

TABLE 1-continued
Structure Formula
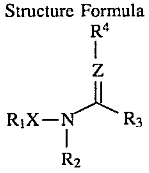
| Compound No. | $R_1X$ | $R_2$ | $R_3$ | Z | $R_4$ | Physical Properties [ ] m.p. °C. |
|---|---|---|---|---|---|---|
| 56 | " | 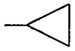 | H | " | " | |
| 57 | 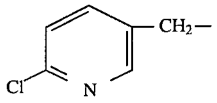 | 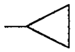 | $CH_3$ | N | CN | $n_D^{25}$ 1.5825 |
| 58 | " | " | $C_2H_5$ | " | " | |
| 59 | " | $CH_2OCH_3$ | H | " | " | |
| 60 | " | " | $CH_3$ | " | " | $n_D^{25.5}$ 1.5711 |
| 61 | " | $CH_2SCH_3$ | H | " | " | |
| 62 | " | " | $CH_3$ | " | " | $n_D^{25}$ 1.5828 |
| 63 | " | $CH_2COOC_2H_5$ | H | " | " | |
| 64 | " | " | $CH_3$ | " | " | $n_D^{25}$ 1.5475 |
| 65 | " | 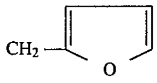 | H | " | " | |
| 66 | " | " | $CH_3$ | " | " | $n_D^{25.5}$ 1.5928 |
| 67 | " | 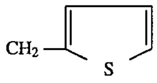 | H | " | " | |
| 68 | " | " | $CH_3$ | " | " | $n_D^{25.5}$ 1.6155 |
| 69 | " | 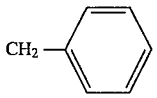 | H | " | " | |
| 70 | " | " | $CH_3$ | " | " | $n_D^{24.5}$ 1.6093 |
| 71 | " | 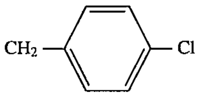 | H | " | " | |

TABLE 1-continued
Structure Formula
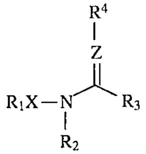
| Compound No. | $R_1X$ | $R_2$ | $R_3$ | Z | $R_4$ | Physical Properties [ ] m.p. °C. |
|---|---|---|---|---|---|---|
| 72 | 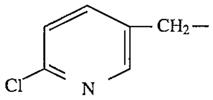 | 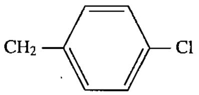 | $CH_3$ | N | CN | [112–114] |
| 73 | " | $CH_2CH=CH_2$ | H | " | " | $n_D^{25}$ 1.5841 |
| 74 | " | " | $CH_3$ | " | " | $n_D^{25}$ 1.5809 |
| 75 | " | $CH_2C=CH$ | H | " | " | |
| 76 | " | " | $CH_3$ | " | " | $n_D^{25.5}$ 1.5730 |
| 77 | " | $CH_2CN$ | H | " | " | |
| 78 | " | " | $CH_3$ | " | " | [127–128] |
| 79 | " | 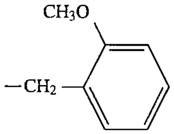 | H | " | " | |
| 80 | " | " | $CH_3$ | " | " | [124–127] |
| 81 | " | 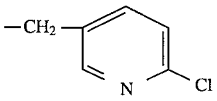 | H | " | " | |
| 82 | " | " | $CH_3$ | " | " | $n_D^{24.5}$ 1.6045 |
| 83 | " | 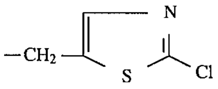 | H | " | " | |
| 84 | " | " | $CH_3$ | " | " | $n_D^{25.5}$ 1.6092 |
| 85 | " | 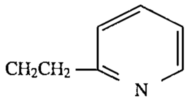 | H | " | " | |

TABLE 1-continued
Structure Formula
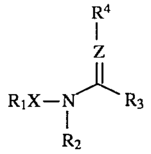
| Compound No. | $R_1X$ | $R_2$ | $R_3$ | Z | $R_4$ | Physical Properties [ ] m.p. °C. |
|---|---|---|---|---|---|---|
| 86 | 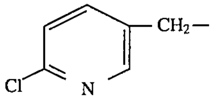 | 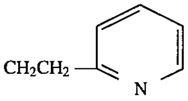 | $CH_3$ | N | CN | $n_D^{25.5}$ 1.5910 |
| 87 | " | 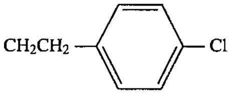 | H | " | " | |
| 88 | " | " | $CH_3$ | " | " | $n_D^{25.5}$ 1.6162 |
| 89 | " | 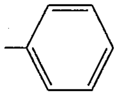 | H | " | " | |
| 90 | " | " | $CH_3$ | " | " | [115–117] |
| 91 | " | $OCH_3$ | H | " | " | |
| 92 | " | " | $CH_3$ | " | " | [110–112] |
| 93 | " | CHO | H | " | " | |
| 94 | " | " | $CH_3$ | " | " | |
| 95 | " | $COCH_3$ | H | " | " | $n_D^{25.5}$ 1.5475 |
| 96 | " | " | $CH_3$ | " | " | [84–86] |
| 97 | " | $SO_2CH_3$ | H | " | " | [160–163] |
| 98 | " | " | $CH_3$ | " | " | |
| 99 | " | 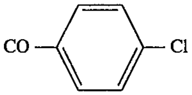 | H | " | " | |
| 100 | " | " | $CH_3$ | " | " | [112–114] |
| 101 | 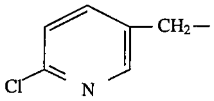 | $COOC_2H_5$ | H | N | CN | |

TABLE 1-continued
Structure Formula
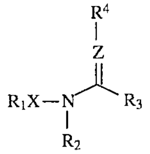
| Compound No. | $R_1X$ | $R_2$ | $R_3$ | Z | $R_4$ | Physical Properties [ ] m.p. °C. |
|---|---|---|---|---|---|---|
| 102 | " | " | $CH_3$ | " | " | $n_D^{25}$ 1.5540 |
| 103 | " | $CONH_2$ | H | " | " | |
| 104 | " | " | $CH_3$ | " | " | |
| 105 | " | 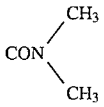 | H | " | " | |
| 106 | " | " | $CH_3$ | " | " | [89-91] |
| 107 | " | $CONHCH_3$ | H | " | " | |
| 108 | " | " | $CH_3$ | " | " | |
| 109 | " | $CSNHCH_3$ | H | " | " | |
| 110 | " | " | $CH_3$ | " | " | |
| 111 | 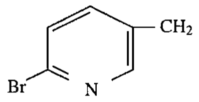 | H | $CH_3$ | " | " | |
| 112 | " | $CH_3$ | " | " | " | |
| 113 | 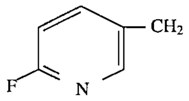 | H | " | " | " | |
| 114 | " | $CH_3$ | " | " | " | |
| 115 | 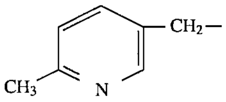 | H | " | " | " | [83-85] |

TABLE 1-continued
Structure Formula
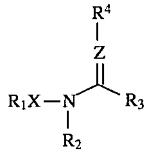
| Compound No. | $R_1X$ | $R_2$ | $R_3$ | Z | $R_4$ | Physical Properties [ ] m.p. °C. |
|---|---|---|---|---|---|---|
| 116 | 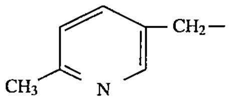 | $CH_3$ | $CH_3$ | N | CN | [76–78] |
| 117 | 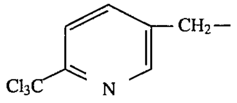 | H | " | " | " | |
| 118 | " | $CH_3$ | " | " | " | [145–147] |
| 119 | 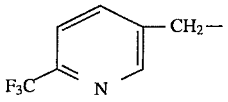 | H | " | " | " | |
| 120 | " | $CH_3$ | " | " | " | $n_D^{25}$ 1.5202 |
| 121 | 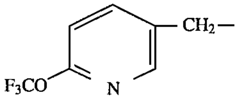 | H | " | " | " | |
| 122 | " | $CH_3$ | " | " | " | |
| 123 | 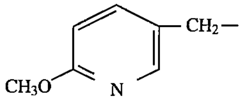 | H | " | " | " | |
| 124 | " | $CH_3$ | " | " | " | $n_D^{25.5}$ 1.5580 |
| 125 | 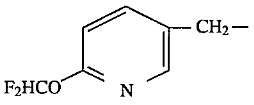 | H | " | " | " | |

TABLE 1-continued
Structure Formula
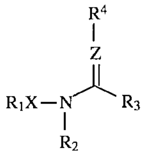
| Compound No. | $R_1X$ | $R_2$ | $R_3$ | Z | $R_4$ | Physical Properties [ ] m.p. °C. |
|---|---|---|---|---|---|---|
| 126 | " | $CH_3$ | " | " | " | |
| 127 | 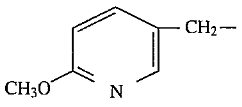 | H | " | " | " | |
| 128 | " | $CH_3$ | " | " | " | |
| 129 | 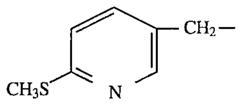 | H | " | " | " | [162–163] |
| 130 | " | $CH_3$ | " | " | " | [105–107] |
| 131 | 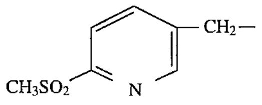 | H | $CH_3$ | N | CN | |
| 132 | " | $CH_3$ | " | " | " | [138–139] |
| 133 | 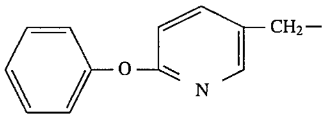 | H | " | " | " | |
| 134 | " | $CH_3$ | " | " | " | $n_D^{25}$ 1.5841 |
| 135 | 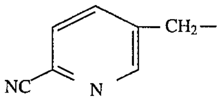 | H | " | " | " | |
| 136 | " | $CH_3$ | " | " | " | [107–109] |

TABLE 1-continued
Structure Formula
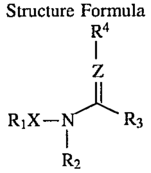
| Compound No. | $R_1X$ | $R_2$ | $R_3$ | Z | $R_4$ | Physical Properties [ ] m.p. °C. |
|---|---|---|---|---|---|---|
| 137 | 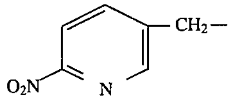 | H | " | " | " | |
| 138 | " | $CH_3$ | " | " | " | |
| 139 | 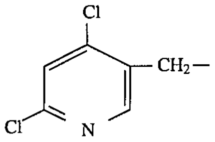 | H | " | " | " | |
| 140 | " | $CH_3$ | " | " | " | |
| 141 | 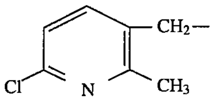 | H | " | " | " | |
| 142 | " | $CH_3$ | " | " | " | |
| 143 | 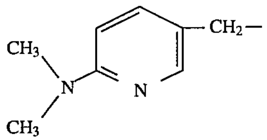 | H | " | " | " | [122–124] |
| 144 | " | $CH_3$ | " | " | " | [110–113] |
| 145 | 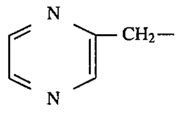 | H | $CH_3$ | N | CN | [66–68] |
| 146 | " | $CH_3$ | " | " | " | $n_D^{24.5}$ 1.5790 |

TABLE 1-continued
Structure Formula
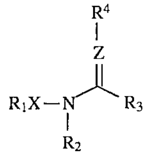
| Compound No. | $R_1X$ | $R_2$ | $R_3$ | Z | $R_4$ | Physical Properties [ ] m.p. °C. |
|---|---|---|---|---|---|---|
| 147 | 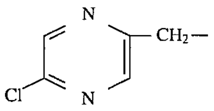 | H | " | " | " | |
| 148 | " | $CH_3$ | " | " | " | [94–96] |
| 149 | 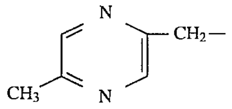 | H | " | " | " | [130–132] |
| 150 | " | $CH_3$ | " | " | " | $n_D^{25}$ 1.5612 |
| 151 | 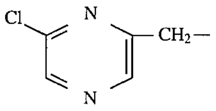 | H | " | " | " | [96–99] |
| 152 | " | $CH_3$ | " | " | " | $n_D^{25.5}$ 1.5800 |
| 153 | 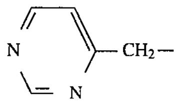 | H | " | " | " | |
| 154 | " | $CH_3$ | " | " | " | |
| 155 | 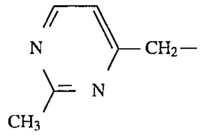 | H | " | " | " | |

TABLE 1-continued
Structure Formula
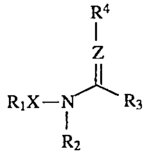
| Compound No. | $R_1X$ | $R_2$ | $R_3$ | Z | $R_4$ | Physical Properties [ ] m.p. °C. |
|---|---|---|---|---|---|---|
| 156 | 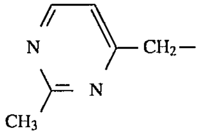 | $CH_3$ | $CH_3$ | N | CN | |
| 157 | 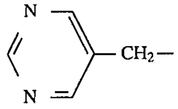 | H | " | " | " | |
| 158 | " | $CH_3$ | " | " | " | |
| 159 | 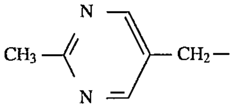 | H | " | " | " | |
| 160 | " | $CH_3$ | " | " | " | |
| 161 | 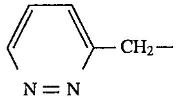 | H | " | " | " | |
| 162 | " | $CH_3$ | " | " | " | |
| 163 | 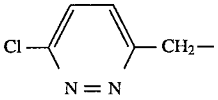 | H | " | " | " | [115-117] |
| 164 | " | $CH_3$ | " | " | " | $n_D^{23}$ 1.5717 |

TABLE 1-continued
Structure Formula
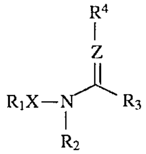
| Compound No. | $R_1X$ | $R_2$ | $R_3$ | Z | $R_4$ | Physical Properties [ ] m.p. °C. |
|---|---|---|---|---|---|---|
| 165 | 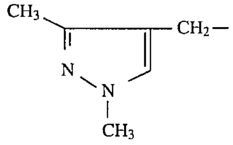 | H | " | " | " | [104–106] |
| 166 | " | $CH_3$ | " | " | " | |
| 167 | 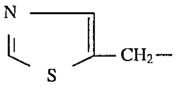 | H | $CH_3$ | N | CN | |
| 168 | " | $CH_3$ | " | " | " | |
| 169 | 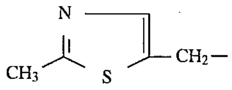 | H | " | " | " | [112–114] |
| 170 | " | $CH_3$ | " | " | " | $n_D^{25}$ 1.5413 |
| 171 | 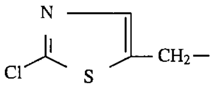 | H | " | " | " | [122–124] |
| 172 | " | $CH_3$ | " | " | " | [143–144] |
| 173 | " | " | $C_2H_5$ | " | " | $n_D^{25}$ 1.5575 |
| 174 | " | $C_2H_5$ | $CH_3$ | " | " | [63–70] |
| 175 | 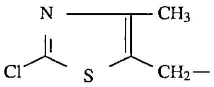 | H | " | " | " | [149–151] |
| 176 | " | $CH_3$ | " | " | " | |

TABLE 1-continued
Structure Formula
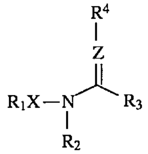
| Compound No. | $R_1X$ | $R_2$ | $R_3$ | Z | $R_4$ | Physical Properties [ ] m.p. °C. |
|---|---|---|---|---|---|---|
| 177 | 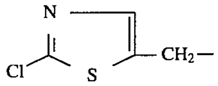 | H | H | " | " | [179–183] |
| 178 | " | $CH_3$ | " | " | " | $n_D^{25}$ 1.5952 |
| 179 | 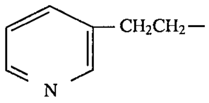 | H | $CH_3$ | N | CN | |
| 180 | " | $CH_3$ | " | " | " | |
| 181 | 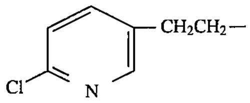 | H | " | " | " | |
| 182 | " | $CH_3$ | " | " | " | |
| 183 | 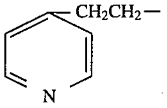 | H | " | " | " | |
| 184 | " | $CH_3$ | " | " | " | |
| 185 | 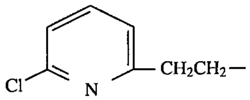 | H | " | " | " | |
| 186 | " | $CH_3$ | " | " | " | |

TABLE 1-continued
Structure Formula
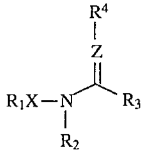
| Compound No. | $R_1X$ | $R_2$ | $R_3$ | Z | $R_4$ | Physical Properties [ ] m.p. °C. |
|---|---|---|---|---|---|---|
| 187 | 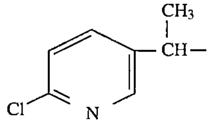 | H | " | " | " | |
| 188 | " | $CH_3$ | " | " | " | [106–109] |
| 189 | 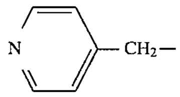 | H | $CH_3$ | " | " | [90–92] |
| 190 | 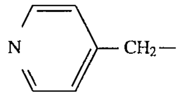 | $CH_3$ | $CH_3$ | N | CN | [102–103] |
| 191 | 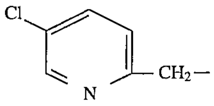 | H | " | " | " | |
| 192 | " | $CH_3$ | " | " | " | |
| 193 | 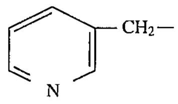 | H | H | " | " | |
| 194 | " | " | $CH_3$ | " | " | [127–129] |
| 195 | " | " | $CH_2Cl$ | " | " | |
| 196 | " | " | $CH_2F$ | " | " | |
| 197 | " | " | $C_2H_5$ | " | " | |
| 198 | " | " | 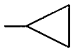 | " | " | |

TABLE 1-continued

Structure Formula

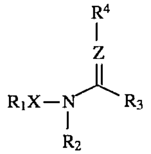

| Compound No. | $R_1X$ | $R_2$ | $R_3$ | Z | $R_4$ | Physical Properties [ ] m.p. °C. |
|---|---|---|---|---|---|---|
| 199 | " | " | $CH_2SCH_3$ | " | " | |
| 200 | " | " | $CH_2OCH_3$ | " | " | |
| 201 | 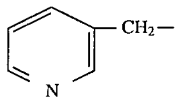 | H | $C_3H_7(n)$ | N | CN | $n_D^{25.5}$ 1.5528 |
| 202 | " | $CH_3$ | H | " | " | |
| 203 | " | " | $CH_3$ | " | " | $n_D^{25.5}$ 1.5798 |
| 204 | " | " | $CH_2Cl$ | " | " | |
| 205 | " | " | $CH_2F$ | " | " | |
| 206 | " | H | $C_2H_5$ | " | " | $n_D^{25.5}$ 1.5657 |
| 207 | " | " | 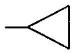 | " | " | |
| 208 | " | " | $CH_2SCH_3$ | " | " | |
| 209 | " | " | $CH_2OCH_3$ | " | " | |
| 210 | " | " | $C_3H_7(i)$ | " | " | |
| 211 | " | " | $C_4H_9(t)$ | " | " | |
| 212 | 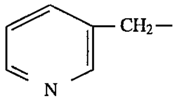 | $C_2H_5$ | H | N | CN | |
| 213 | " | " | $CH_3$ | " | " | $n_D^{24.5}$ 1.5665 |
| 214 | " | " | $CH_2Cl$ | " | " | |
| 215 | " | " | $C_2H_5$ | " | " | |
| 216 | " | $C_3H_7(i)$ | H | " | " | |
| 217 | " | " | $CH_3$ | " | " | |
| 218 | " | " | $C_2H_5$ | " | " | |
| 219 | " | $COCH_3$ | H | " | " | |
| 220 | " | " | $CH_3$ | " | " | |
| 221 | " | $SO_2CH_3$ | H | " | " | |
| 222 | " | " | $CH_3$ | " | " | |

TABLE 1-continued
Structure Formula
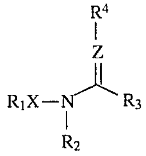
| Compound No. | $R_1X$ | $R_2$ | $R_3$ | Z | $R_4$ | Physical Properties [ ] m.p. °C. |
|---|---|---|---|---|---|---|
| 223 | 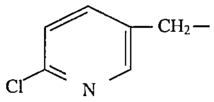 | H | H | N | $NO_2$ | |
| 224 | " | " | $CH_3$ | " | " | |
| 225 | " | " | $CH_2Cl$ | " | " | |
| 226 | " | " | $CH_2F$ | " | " | |
| 227 | " | " | $C_2H_5$ | " | " | |
| 228 | " | " | 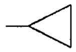 | " | " | |
| 229 | " | " | $CH_2SCH_3$ | " | " | |
| 230 | " | " | $CH_2OCH_3$ | " | " | |
| 231 | " | " | $C_3H_7(i)$ | " | " | |
| 232 | " | " | $C_4H_9(t)$ | " | " | |
| 233 | " | " | $CH{=}CH_2$ | " | " | |
| 234 | " | " | 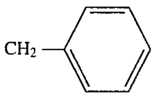 | " | " | |
| 235 | 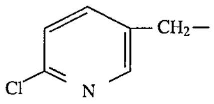 | $CH_3$ | H | N | $NO_2$ | |
| 236 | " | " | $CH_3$ | " | " | $n_D^{25}$ 1.5808 |
| 237 | " | " | $CH_2Cl$ | " | " | |
| 238 | " | " | $CH_2F$ | " | " | |
| 239 | " | " | $C_2H_5$ | " | " | |
| 240 | " | " | 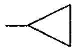 | " | " | |
| 241 | " | " | $CH_2SCH_3$ | " | " | |
| 242 | " | " | $CH_2OCH_3$ | " | " | |

TABLE 1-continued
Structure Formula
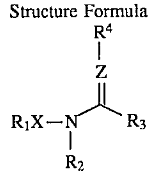
| Compound No. | $R_1X$ | $R_2$ | $R_3$ | Z | $R_4$ | Physical Properties [ ] m.p. °C. |
|---|---|---|---|---|---|---|
| 243 | " | " | $C_3H_7(n)$ | " | " | |
| 244 | " | " | $C_4H_9(t)$ | " | " | |
| 245 | " | " | $CH=CH_2$ | " | " | |
| 246 | " | " | 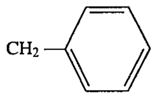 | " | " | |
| 247 | 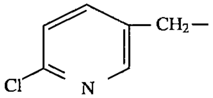 | $C_2H_5$ | H | N | $NO_2$ | |
| 248 | " | " | $CH_3$ | " | " | |
| 249 | " | " | $C_2H_5$ | " | " | |
| 250 | " | $C_3H_7(i)$ | H | " | " | |
| 251 | " | " | $CH_3$ | " | " | |
| 252 | " | " | $C_2H_5$ | " | " | |
| 253 | " | 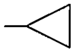 | H | " | " | |
| 254 | " | " | $CH_3$ | " | " | |
| 255 | " | " | $C_2H_5$ | " | " | |
| 256 | " | $COCH_3$ | H | " | " | |
| 257 | " | " | $CH_3$ | " | " | |
| 258 | " | $SO_2CH_3$ | H | " | " | |
| 259 | " | " | $CH_3$ | " | " | |
| 260 | 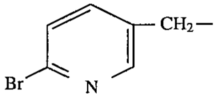 | H | $CH_3$ | N | $NO_2$ | |
| 261 | " | $CH_3$ | " | " | " | |

TABLE 1-continued
Structure Formula
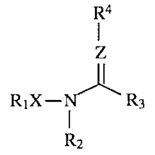
| Compound No. | $R_1X$ | $R_2$ | $R_3$ | Z | $R_4$ | Physical Properties [ ] m.p. °C. |
|---|---|---|---|---|---|---|
| 262 | 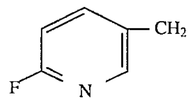 | H | " | " | " | |
| 263 | " | $CH_3$ | " | " | " | |
| 264 | 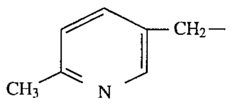 | H | " | " | " | |
| 265 | " | $CH_3$ | " | " | " | |
| 266 | 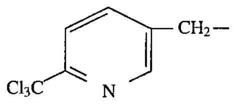 | H | " | " | " | |
| 267 | " | $CH_3$ | " | " | " | |
| 268 | 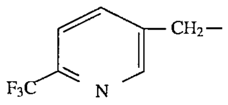 | H | " | " | " | |
| 269 | " | $CH_3$ | " | " | " | |
| 270 | 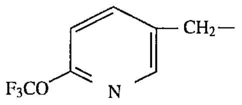 | H | " | " | " | |
| 271 | " | $CH_3$ | " | " | " | |

TABLE 1-continued
Structure Formula
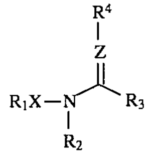
| Compound No. | $R_1X$ | $R_2$ | $R_3$ | Z | $R_4$ | Physical Properties [ ] m.p. °C. |
|---|---|---|---|---|---|---|
| 272 | 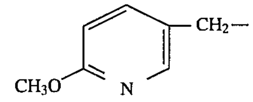 | H | $CH_3$ | N | $NO_2$ | |
| 273 | " | $CH_3$ | " | " | " | |
| 274 | 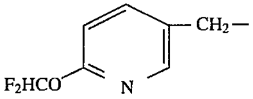 | H | " | " | " | |
| 275 | " | $CH_3$ | " | " | " | |
| 276 | 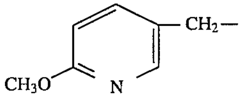 | H | " | " | " | |
| 277 | " | $CH_3$ | " | " | " | |
| 278 | 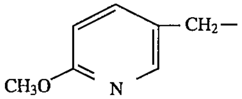 | H | " | " | " | |
| 279 | " | $CH_3$ | " | " | " | |
| 280 | 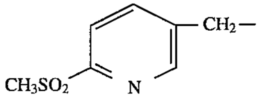 | H | " | " | " | |
| 281 | " | $CH_3$ | " | " | " | |

TABLE 1-continued
Structure Formula
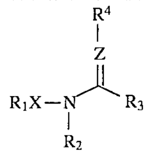
| Compound No. | $R_1X$ | $R_2$ | $R_3$ | Z | $R_4$ | Physical Properties [ ] m.p. °C. |
|---|---|---|---|---|---|---|
| 282 | 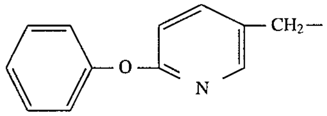 | H | " | " | " | |
| 283 | " | $CH_3$ | " | " | " | |
| 284 | 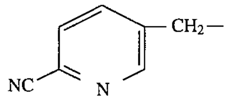 | H | $CH_3$ | N | $NO_2$ | |
| 285 | " | $CH_3$ | " | " | " | |
| 286 | 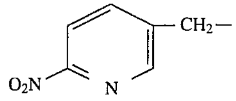 | H | " | " | " | |
| 287 | " | $CH_3$ | " | " | " | |
| 288 | 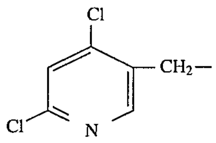 | H | " | " | " | |
| 289 | " | $CH_3$ | " | " | " | |
| 290 | 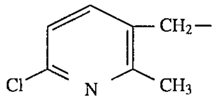 | H | " | " | " | |
| 291 | " | $CH_3$ | " | " | " | |

TABLE 1-continued
Structure Formula
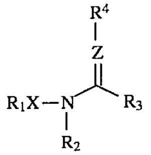
| Compound No. | $R_1X$ | $R_2$ | $R_3$ | Z | $R_4$ | Physical Properties [ ] m.p. °C. |
|---|---|---|---|---|---|---|
| 292 | 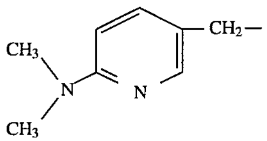 | H | " | " | " | |
| 293 | " | $CH_3$ | " | " | " | |
| 294 | 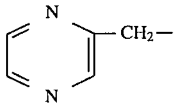 | H | $CH_3$ | N | $NO_2$ | |
| 295 | " | $CH_3$ | " | " | " | |
| 296 | 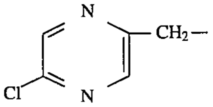 | H | " | " | " | |
| 297 | " | $CH_3$ | " | " | " | |
| 298 | 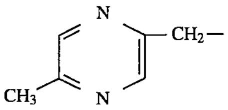 | H | " | " | " | |
| 299 | " | $CH_3$ | " | " | " | |
| 300 | 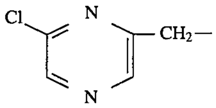 | H | " | " | " | |
| 301 | " | $CH_3$ | " | " | " | |

TABLE 1-continued
Structure Formula
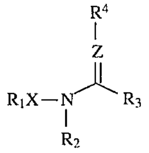
| Compound No. | $R_1X$ | $R_2$ | $R_3$ | Z | $R_4$ | Physical Properties [ ] m.p. °C. |
|---|---|---|---|---|---|---|
| 302 | 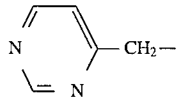 | H | " | " | " | |
| 303 | " | $CH_3$ | " | " | " | |
| 304 | 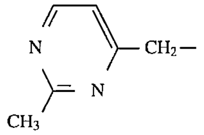 | H | " | " | " | |
| 305 | 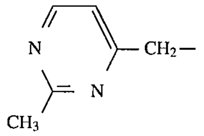 | $CH_3$ | $CH_3$ | N | $NO_2$ | |
| 306 | 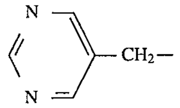 | H | " | " | " | |
| 307 | " | $CH_3$ | " | " | " | |
| 308 | 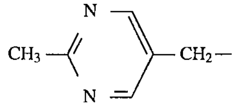 | H | " | " | " | |
| 309 | " | $CH_3$ | " | " | " | |

TABLE 1-continued
Structure Formula
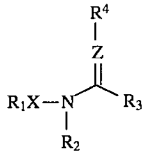
| Compound No. | $R_1X$ | $R_2$ | $R_3$ | Z | $R_4$ | Physical Properties [ ] m.p. °C. |
|---|---|---|---|---|---|---|
| 310 | 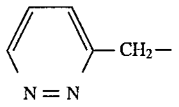 | H | " | " | " | |
| 311 | " | $CH_3$ | " | " | " | |
| 312 | 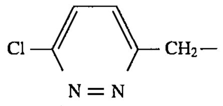 | H | " | " | " | |
| 313 | " | $CH_3$ | " | " | " | |
| 314 | 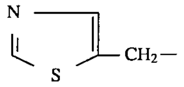 | H | $CH_3$ | N | $NO_2$ | |
| 315 | " | $CH_3$ | " | " | " | |
| 316 | 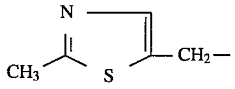 | H | " | " | " | |
| 317 | " | $CH_3$ | " | " | " | |
| 318 | 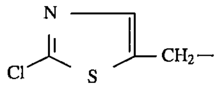 | H | " | " | " | |
| 319 | " | $CH_3$ | " | " | " | |
| 320 | " | " | $C_2H_5$ | " | " | |
| 321 | " | $C_2H_5$ | $CH_3$ | " | " | |
| 322 | 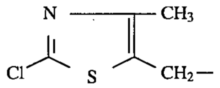 | H | " | " | " | |

TABLE 1-continued
Structure Formula
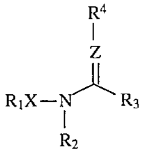
| Compound No. | $R_1X$ | $R_2$ | $R_3$ | Z | $R_4$ | Physical Properties [ ] m.p. °C. |
|---|---|---|---|---|---|---|
| 323 | " | $CH_3$ | " | " | " | |
| 324 | 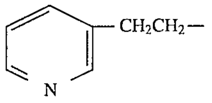 | H | $CH_3$ | N | $NO_2$ | |
| 325 | " | $CH_3$ | " | " | " | |
| 326 | 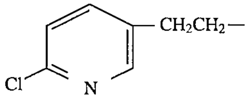 | H | " | " | " | |
| 327 | " | $CH_3$ | " | " | " | |
| 328 | 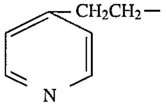 | H | " | " | " | |
| 329 | " | $CH_3$ | " | " | " | |
| 330 | 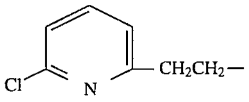 | H | " | " | " | |
| 331 | " | $CH_3$ | " | " | " | |
| 332 | 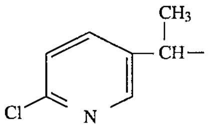 | H | " | " | " | |
| 333 | " | $CH_3$ | " | " | " | |

TABLE 1-continued
Structure Formula
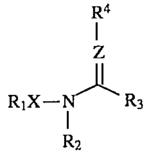
| Compound No. | $R_1X$ | $R_2$ | $R_3$ | Z | $R_4$ | Physical Properties [ ] m.p. °C. |
|---|---|---|---|---|---|---|
| 334 | 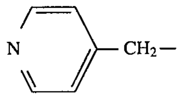 | H | " | " | " | |
| 335 | " | $CH_3$ | " | " | " | |
| 336 | 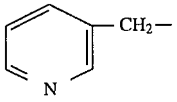 | H | H | N | $NO_2$ | |
| 337 | " | " | $CH_3$ | " | " | |
| 338 | " | " | $C_2H_5$ | " | " | |
| 339 | " | " | $CH_2Cl$ | " | " | |
| 340 | " | " | $CH_2F$ | " | " | |
| 341 | " | " | 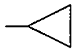 | " | " | |
| 342 | " | " | $CH_2SCH_3$ | " | " | |
| 343 | " | " | $CH_2OCH_3$ | " | " | |
| 344 | 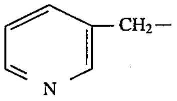 | $CH_3$ | H | N | $NO_2$ | |
| 345 | " | " | $CH_3$ | " | " | |
| 346 | " | " | $CH_2Cl$ | " | " | |
| 347 | " | " | $CH_2F$ | " | " | |
| 348 | " | " | $C_2H_5$ | " | " | |
| 349 | " | " | 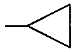 | " | " | |
| 350 | " | " | $CH_2SCH_3$ | " | " | |
| 351 | " | " | $CH_2OCH_3$ | " | " | |

TABLE 1-continued

Structure Formula

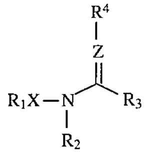

| Compound No. | $R_1X$ | $R_2$ | $R_3$ | Z | $R_4$ | Physical Properties [ ] m.p. °C. |
|---|---|---|---|---|---|---|
| 352 | " | " | $C_3H_7(i)$ | " | " | |
| 353 | " | " | $C_4H_9(t)$ | " | " | |
| 354 | 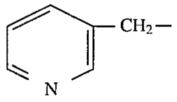 | $C_2H_5$ | H | N | $NO_2$ | |
| 355 | " | " | $CH_3$ | " | " | |
| 356 | " | " | $CH_2Cl$ | " | " | |
| 357 | " | " | $C_2H_5$ | " | " | |
| 358 | " | $C_3H_7(i)$ | H | " | " | |
| 359 | " | " | $CH_3$ | " | " | |
| 360 | " | " | $C_2H_5$ | " | " | |
| 361 | " | $COCH_3$ | H | " | " | |
| 362 | " | " | $CH_3$ | " | " | |
| 363 | " | $SO_2CH_3$ | H | " | " | |
| 364 | " | " | $CH_3$ | " | " | |
| 365 | 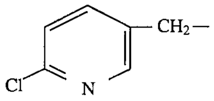 | H | H | CH | $NO_2$ | [116–118] |
| 366 | " | " | $CH_3$ | " | " | [133–135] |
| 367 | " | " | $CH_2Cl$ | " | " | |
| 368 | " | " | $C_2H_5$ | " | " | [95–98] |
| 369 | " | " | $C_3H_7(i)$ | " | " | [150–152] |
| 370 | " | " | $C_4H_7(t)$ | " | " | |
| 371 | " | " | $CH{=}CH_2$ | " | " | |
| 372 | " | " | $CH{=}CHCH_3$ | " | " | |
| 373 | " | " | $CH_2CN$ | " | " | |
| 374 | " | " | $CH_2NO_2$ | " | " | |
| 375 | " | " | $CH_2COOC_2H_5$ | " | " | |
| 376 | 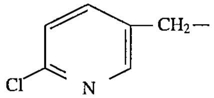 | H | 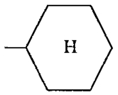 | CH | $NO_2$ | |

TABLE 1-continued
Structure Formula
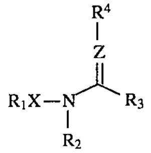
| Compound No. | $R_1X$ | $R_2$ | $R_3$ | Z | $R_4$ | Physical Properties [ ] m.p. °C. |
|---|---|---|---|---|---|---|
| 377 | " | " | 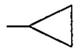 | " | " | |
| 378 | " | " | 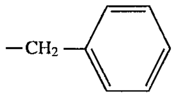 | " | " | |
| 379 | " | " | 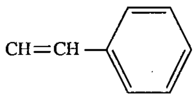 | " | " | |
| 380 | " | $CH_3$ | H | " | " | |
| 381 | " | " | $CH_3$ | " | " | [79–82] |
| 382 | " | " | $CH_2Cl$ | " | " | |
| 383 | " | " | $C_2H_5$ | " | " | [101–104] |
| 384 | " | " | $C_3H_7(i)$ | " | " | |
| 385 | " | " | $C_4H_7(t)$ | " | " | |
| 386 | " | " | $CH=CH_2$ | " | " | |
| 387 | " | " | $CH=CHCH_3$ | " | " | |
| 388 | 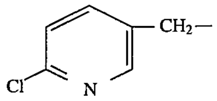 | $CH_3$ | $CH_2CN$ | CH | $NO_2$ | |
| 389 | " | " | $CH_2NO_2$ | " | " | |
| 390 | " | " | $CH_2COOC_2H_5$ | " | " | |
| 391 | " | " | 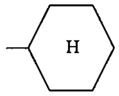 | " | " | |
| 392 | " | " | 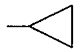 | " | " | |

TABLE 1-continued
Structure Formula
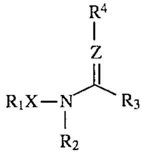
| Compound No. | $R_1X$ | $R_2$ | $R_3$ | Z | $R_4$ | Physical Properties [ ] m.p. °C. |
|---|---|---|---|---|---|---|
| 393 | " | " | 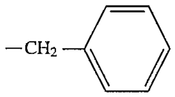 | " | " | |
| 394 | " | " | 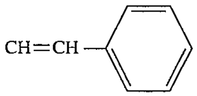 | " | " | |
| 395 | " | $C_2H_5$ | H | " | " | |
| 396 | " | " | $CH_3$ | " | " | |
| 397 | " | " | $C_2H_5$ | " | " | |
| 398 | " | $C_3H_7$(i) | H | " | " | |
| 399 | " | " | $CH_3$ | " | " | |
| 400 | 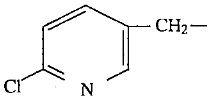 | $C_3H_7$(i) | $C_2H_5$ | CH | $NO_2$ | |
| 401 | " | 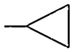 | H | " | " | |
| 402 | " | " | $CH_3$ | " | " | |
| 403 | " | " | $C_2H_5$ | " | " | |
| 404 | " | $CH_2CH=CH_2$ | H | " | " | |
| 405 | " | " | $CH_3$ | " | " | |
| 406 | " | " | $C_2H_5$ | " | " | |
| 407 | " | 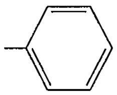 | H | " | " | |
| 408 | " | " | $CH_3$ | " | " | |
| 409 | " | " | $C_2H_5$ | " | " | |
| 410 | " | CHO | H | " | " | |
| 411 | " | " | $CH_3$ | " | " | |

TABLE 1-continued
Structure Formula
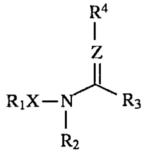
| Compound No. | $R_1X$ | $R_2$ | $R_3$ | Z | $R_4$ | Physical Properties [ ] m.p. °C. |
|---|---|---|---|---|---|---|
| 412 | 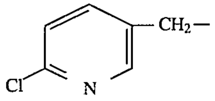 | CHO | $C_2H_5$ | CH | $NO_2$ | |
| 413 | " | $COCH_3$ | H | " | " | |
| 414 | " | " | $CH_3$ | " | " | |
| 415 | " | " | $C_2H_5$ | " | " | |
| 416 | " | $SO_2CH_3$ | H | " | " | |
| 417 | " | " | $CH_3$ | " | " | |
| 418 | " | " | $C_2H_5$ | " | " | |
| 419 | " | $COOC_2H_5$ | H | " | " | |
| 420 | " | " | $CH_3$ | " | " | |
| 421 | " | " | $C_2H_5$ | " | " | |
| 422 | " | $OC_2H_5$ | H | " | " | |
| 423 | " | " | $CH_3$ | " | " | |
| 424 | " | " | $C_2H_5$ | " | " | |
| 425 | " | $CH_2C{=}CH$ | H | " | " | |
| 426 | " | " | $CH_3$ | " | " | |
| 427 | " | " | $C_2H_5$ | " | " | |
| 428 | 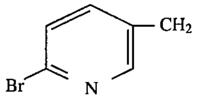 | H | $CH_3$ | CH | $NO_2$ | |
| 429 | " | $CH_3$ | " | " | " | |
| 430 | 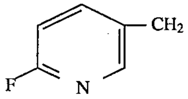 | H | " | " | " | |
| 431 | " | $CH_3$ | " | " | " | |
| 432 | 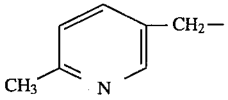 | H | " | " | " | |

TABLE 1-continued
Structure Formula
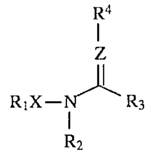
| Compound No. | $R_1X$ | $R_2$ | $R_3$ | Z | $R_4$ | Physical Properties [ ] m.p. °C. |
|---|---|---|---|---|---|---|
| 433 | " | $CH_3$ | " | " | " | |
| 434 | 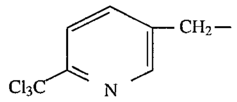 | H | " | " | " | |
| 435 | " | $CH_3$ | " | " | " | |
| 436 | 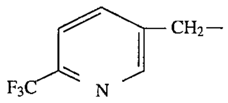 | H | " | " | " | |
| 437 | " | $CH_3$ | " | " | " | |
| 438 | 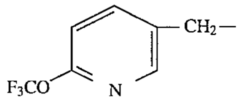 | H | " | " | " | |
| 439 | " | $CH_3$ | " | " | " | |
| 440 | 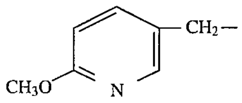 | H | $CH_3$ | CH | $NO_2$ | |
| 441 | " | $CH_3$ | " | " | " | |
| 442 | 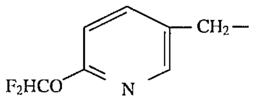 | H | " | " | " | |
| 443 | " | $CH_3$ | " | " | " | |

TABLE 1-continued
Structure Formula
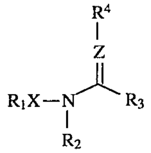
| Compound No. | $R_1X$ | $R_2$ | $R_3$ | Z | $R_4$ | Physical Properties [ ] m.p. °C. |
|---|---|---|---|---|---|---|
| 444 | 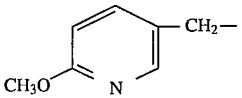 | H | " | " | " | |
| 445 | " | $CH_3$ | " | " | " | |
| 446 | 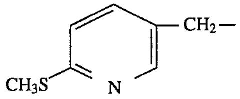 | H | " | " | " | |
| 447 | " | $CH_3$ | " | " | " | |
| 448 | 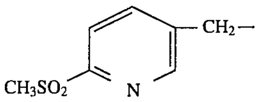 | H | " | " | " | |
| 449 | " | $CH_3$ | " | " | " | |
| 450 | 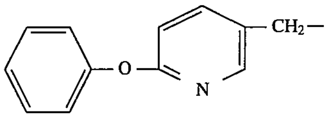 | H | " | " | " | |
| 451 | " | $CH_3$ | " | " | " | |
| 452 | 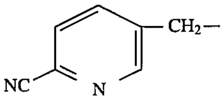 | H | $CH_3$ | CH | $NO_2$ | |
| 453 | " | $CH_3$ | " | " | " | |

TABLE 1-continued
Structure Formula
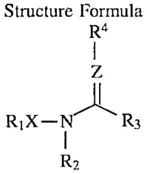
| Compound No. | $R_1X$ | $R_2$ | $R_3$ | Z | $R_4$ | Physical Properties [ ] m.p. °C. |
|---|---|---|---|---|---|---|
| 454 | 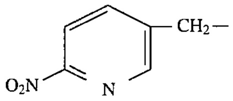 | H | " | " | " | |
| 455 | " | $CH_3$ | " | " | " | |
| 456 | 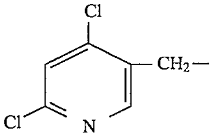 | H | " | " | " | |
| 457 | " | $CH_3$ | " | " | " | |
| 458 | 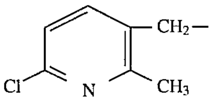 | H | " | " | " | |
| 459 | " | $CH_3$ | " | " | " | |
| 460 | 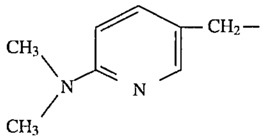 | H | " | " | " | |
| 461 | " | $CH_3$ | " | " | " | |
| 462 | 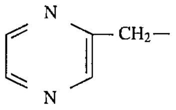 | H | $CH_3$ | CH | $NO_2$ | |
| 463 | " | $CH_3$ | " | " | " | |

TABLE 1-continued
Structure Formula
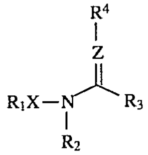
| Compound No. | $R_1X$ | $R_2$ | $R_3$ | Z | $R_4$ | Physical Properties [ ] m.p. °C. |
|---|---|---|---|---|---|---|
| 464 | 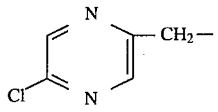 | H | " | " | " | |
| 465 | " | $CH_3$ | " | " | " | |
| 466 | 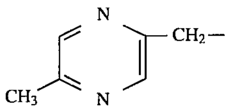 | H | " | " | " | |
| 467 | " | $CH_3$ | " | " | " | |
| 468 | 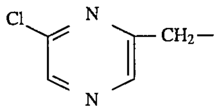 | H | " | " | " | |
| 469 | " | $CH_3$ | " | " | " | |
| 470 | 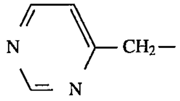 | H | " | " | " | |
| 471 | " | $CH_3$ | " | " | " | |
| 472 | 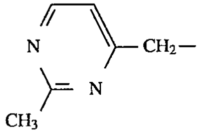 | H | " | " | " | |

TABLE 1-continued
Structure Formula
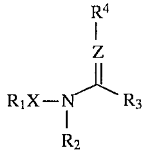
| Compound No. | $R_1X$ | $R_2$ | $R_3$ | Z | $R_4$ | Physical Properties [ ] m.p. °C. |
|---|---|---|---|---|---|---|
| 473 | 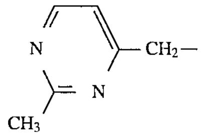 | $CH_3$ | $CH_3$ | CH | $NO_2$ | |
| 474 | 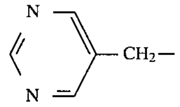 | H | " | " | " | |
| 475 | " | $CH_3$ | " | " | " | |
| 476 | 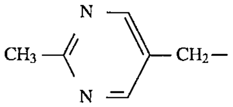 | H | " | " | " | |
| 477 | " | $CH_3$ | " | " | " | |
| 478 | 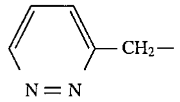 | H | " | " | " | |
| 479 | " | $CH_3$ | " | " | " | |
| 480 | 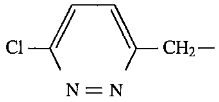 | H | " | " | " | |
| 481 | " | $CH_3$ | " | " | " | |
| 482 | 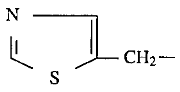 | H | " | " | " | |

TABLE 1-continued
Structure Formula
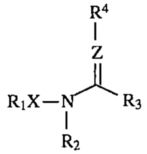
| Compound No. | $R_1X$ | $R_2$ | $R_3$ | Z | $R_4$ | Physical Properties [ ] m.p. °C. |
|---|---|---|---|---|---|---|
| 483 | " | $CH_3$ | " | " | " | |
| 484 | 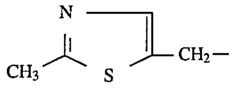 | H | $CH_3$ | CH | $NO_2$ | |
| 485 | " | $CH_3$ | " | " | " | |
| 486 | 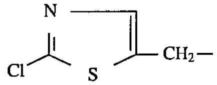 | H | " | " | " | |
| 487 | " | $CH_3$ | " | " | " | |
| 488 | " | " | $C_2H_5$ | " | " | |
| 489 | " | $C_2H_5$ | $CH_3$ | " | " | |
| 490 | 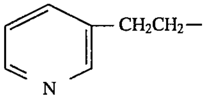 | H | " | " | " | |
| 491 | " | $CH_3$ | " | " | " | |
| 492 | 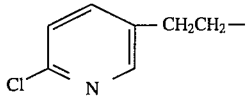 | H | " | " | " | |
| 493 | " | $CH_3$ | " | " | " | |
| 494 | 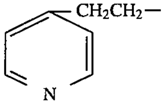 | H | " | " | " | |
| 495 | " | $CH_3$ | " | " | " | |

TABLE 1-continued
Structure Formula
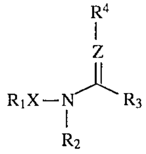
| Compound No. | $R_1X$ | $R_2$ | $R_3$ | Z | $R_4$ | Physical Properties [ ] m.p. °C. |
|---|---|---|---|---|---|---|
| 496 | 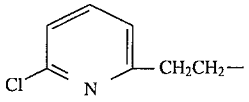 | H | $CH_3$ | CH | $NO_2$ | |
| 497 | " | $CH_3$ | " | " | " | |
| 498 | 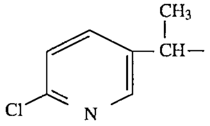 | H | " | " | " | |
| 499 | " | $CH_3$ | " | " | " | |
| 500 | 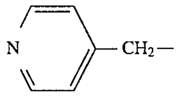 | H | " | " | " | |
| 501 | " | $CH_3$ | " | " | " | |
| 502 | 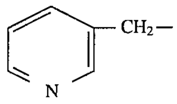 | H | H | CH | $NO_2$ | |
| 503 | " | " | $CH_3$ | " | " | |
| 504 | " | " | $CH_2Cl$ | " | " | |
| 505 | " | " | $C_2H_5$ | " | " | |
| 506 | " | " | $C_3H_7$(i) | " | " | |
| 507 | " | " | $C_4H_9$(t) | " | " | |
| 508 | " | $CH_3$ | H | " | " | |
| 509 | " | " | $CH_3$ | " | " | |
| 510 | " | " | $CH_2Cl$ | " | " | |
| 511 | " | " | $C_2H_5$ | " | " | |
| 512 | " | " | 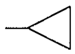 | " | " | |

TABLE 1-continued

Structure Formula

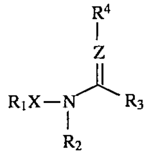

| Compound No. | $R_1X$ | $R_2$ | $R_3$ | Z | $R_4$ | Physical Properties [ ] m.p. °C. |
|---|---|---|---|---|---|---|
| 513 | 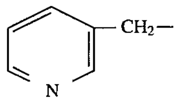 | $CH_3$ | $C_3H_7$(i) | CH | $NO_2$ | |
| 514 | " | " | $C_4H_9$(t) | " | " | |
| 515 | " | $C_2H_5$ | H | " | " | |
| 516 | " | " | $CH_3$ | " | " | |
| 517 | " | " | $C_2H_5$ | " | " | |
| 518 | " | 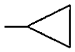 | H | " | " | |
| 519 | " | " | $CH_3$ | " | " | |
| 520 | " | " | $C_2H_5$ | " | " | |
| 521 | " | $COCH_3$ | H | " | " | |
| 522 | " | " | $CH_3$ | " | " | |
| 523 | " | " | $C_2H_5$ | " | " | |
| 524 | " | $SO_2CH_3$ | H | " | " | |
| 525 | " | " | $CH_3$ | " | " | |
| 526 | " | " | $C_2H_5$ | " | " | |
| 527 | 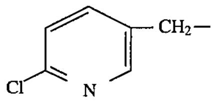 | H | H | CH | CN | |
| 528 | " | " | $CH_3$ | " | " | [95-98] |
| 529 | " | " | $CH_2Cl$ | " | " | |
| 530 | " | " | $C_2H_5$ | " | " | |
| 531 | " | " | $C_3H_7$(i) | " | " | |
| 532 | " | " | $C_4H_9$(t) | " | " | |
| 533 | " | " | $CH=CH_2$ | " | " | |
| 534 | " | " | $CH=CHCH_3$ | " | " | |
| 535 | " | " | $CH_2CN$ | " | " | |
| 536 | " | " | $CH_2NO_2$ | " | " | |
| 537 | " | " | $CH_2COOC_2H_5$ | " | " | |

TABLE 1-continued
Structure Formula
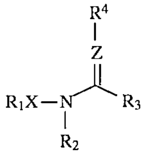
| Compound No. | $R_1X$ | $R_2$ | $R_3$ | Z | $R_4$ | Physical Properties [ ] m.p. °C. |
|---|---|---|---|---|---|---|
| 538 | 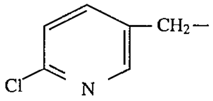 | H | 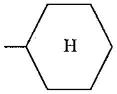 | CH | CN | |
| 539 | " | " | 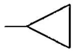 | " | " | |
| 540 | " | " | 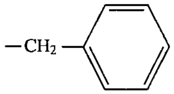 | " | " | |
| 541 | " | " | 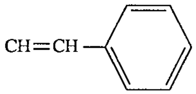 | " | " | |
| 542 | " | $CH_3$ | H | " | " | |
| 543 | " | " | $CH_3$ | " | " | $n_D^{29}$ 1.5941 |
| 544 | " | " | $CH_2Cl$ | " | " | |
| 545 | " | " | $C_2H_5$ | " | " | |
| 546 | " | " | $C_3H_7(i)$ | " | " | |
| 547 | " | " | $C_4H_9(t)$ | " | " | |
| 548 | " | " | $CH=CH_2$ | " | " | |
| 549 | " | " | $CH=CHCH_3$ | " | " | |
| 550 | 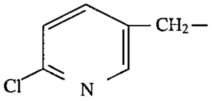 | $CH_3$ | $CH_2CN$ | CH | CN | |
| 551 | " | " | $CH_2NO_2$ | " | " | |
| 552 | " | " | $CH_2COOC_2H_5$ | " | " | |
| 553 | " | " | 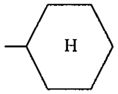 | " | " | |

TABLE 1-continued
Structure Formula
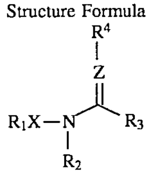
| Compound No. | $R_1X$ | $R_2$ | $R_3$ | Z | $R_4$ | Physical Properties [ ] m.p. °C. |
|---|---|---|---|---|---|---|
| 554 | " | " | 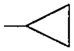 | " | " | |
| 555 | " | " | 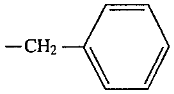 | " | " | |
| 556 | " | " | 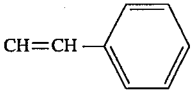 | " | " | |
| 557 | " | $C_2H_5$ | H | " | " | |
| 558 | " | " | $CH_3$ | " | " | |
| 559 | " | " | $C_2H_5$ | " | " | |
| 560 | " | $C_3H_7$(i) | H | " | " | |
| 561 | " | " | $CH_3$ | " | " | |
| 562 | 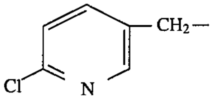 | $C_3H_7$(i) | $C_2H_5$ | CH | CN | |
| 563 | " | 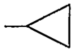 | H | " | " | |
| 564 | " | " | $CH_3$ | " | " | |
| 565 | " | " | $C_2H_5$ | " | " | |
| 566 | " | $CH_2CH{=}CH_2$ | H | " | " | |
| 567 | " | " | $CH_3$ | " | " | |
| 568 | " | " | $C_2H_5$ | " | " | |
| 569 | " | 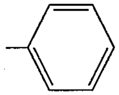 | H | " | " | |

TABLE 1-continued
Structure Formula
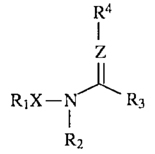
| Compound No. | $R_1X$ | $R_2$ | $R_3$ | Z | $R_4$ | Physical Properties [ ] m.p. °C. |
|---|---|---|---|---|---|---|
| 570 | " | " | $CH_3$ | " | " | |
| 571 | " | " | $C_2H_5$ | " | " | |
| 572 | " | CHO | H | " | " | |
| 573 | " | " | $CH_3$ | " | " | |
| 574 | 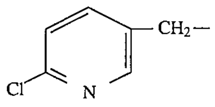 | CHO | $C_2H_5$ | CH | CN | |
| 575 | " | $COCH_3$ | H | " | " | |
| 576 | " | " | $CH_3$ | " | " | |
| 577 | " | " | $C_2H_5$ | " | " | |
| 578 | " | $SO_2CH_3$ | H | " | " | |
| 579 | " | " | $CH_3$ | " | " | |
| 580 | " | " | $C_2H_5$ | " | " | |
| 581 | " | $COOC_2H_5$ | H | " | " | |
| 582 | " | " | $CH_3$ | " | " | |
| 583 | " | " | $C_2H_5$ | " | " | |
| 584 | " | $OC_2H_5$ | H | " | " | |
| 585 | " | " | $CH_3$ | " | " | |
| 586 | " | " | $C_2H_5$ | " | " | |
| 587 | " | $CH_2C{=}CH$ | H | " | " | |
| 588 | " | " | $CH_3$ | " | " | |
| 589 | " | " | $C_2H_5$ | " | " | |
| 590 | 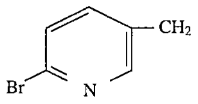 | H | $CH_3$ | CH | CN | |
| 591 | " | $CH_3$ | " | " | " | |
| 592 | 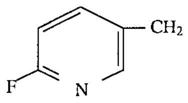 | H | " | " | " | |
| 593 | " | $CH_3$ | " | " | " | |

TABLE 1-continued
Structure Formula
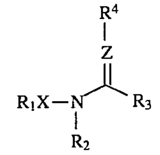
| Compound No. | $R_1X$ | $R_2$ | $R_3$ | Z | $R_4$ | Physical Properties [ ] m.p. °C. |
|---|---|---|---|---|---|---|
| 594 | 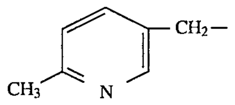 | H | " | " | " | |
| 595 | " | $CH_3$ | " | " | " | |
| 596 | 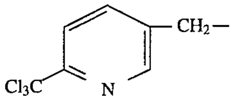 | H | " | " | " | |
| 597 | " | $CH_3$ | " | " | " | |
| 598 | 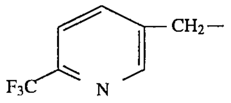 | H | " | " | " | |
| 599 | " | $CH_3$ | " | " | " | |
| 600 | 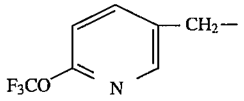 | H | " | " | " | |
| 601 | " | $CH_3$ | " | " | " | |
| 602 | 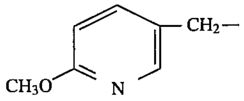 | H | $CH_3$ | CH | CN | |
| 603 | " | $CH_3$ | " | " | " | |

TABLE 1-continued
Structure Formula
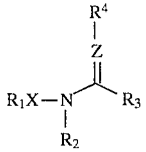
| Compound No. | $R_1X$ | $R_2$ | $R_3$ | Z | $R_4$ | Physical Properties [ ] m.p. °C. |
|---|---|---|---|---|---|---|
| 604 | 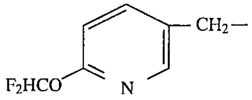 | H | " | " | " | |
| 605 | " | $CH_3$ | " | " | " | |
| 606 | 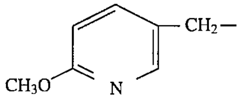 | H | " | " | " | |
| 607 | " | $CH_3$ | " | " | " | |
| 608 | 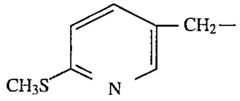 | H | " | " | " | |
| 609 | " | $CH_3$ | " | " | " | |
| 610 | 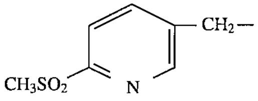 | H | " | " | " | |
| 611 | " | $CH_3$ | " | " | " | |
| 612 | 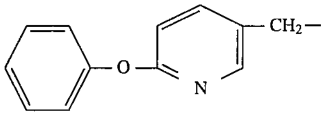 | H | " | " | " | |
| 613 | " | $CH_3$ | " | " | " | |

TABLE 1-continued
Structure Formula
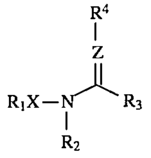
| Compound No. | $R_1X$ | $R_2$ | $R_3$ | Z | $R_4$ | Physical Properties [ ] m.p. °C. |
|---|---|---|---|---|---|---|
| 614 | 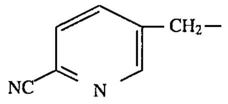 | H | $CH_3$ | CH | CN | |
| 615 | " | $CH_3$ | " | " | " | |
| 616 | 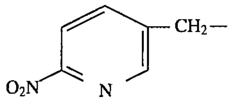 | H | " | " | " | |
| 617 | " | $CH_3$ | " | " | " | |
| 618 | 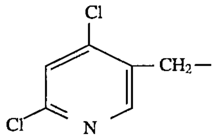 | H | " | " | " | |
| 619 | " | $CH_3$ | " | " | " | |
| 620 | 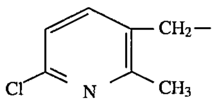 | H | " | " | " | |
| 621 | " | $CH_3$ | " | " | " | |
| 622 | 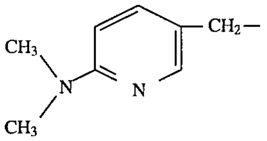 | H | " | " | " | |
| 623 | " | $CH_3$ | " | " | " | |

TABLE 1-continued
Structure Formula
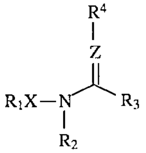
| Compound No. | $R_1X$ | $R_2$ | $R_3$ | Z | $R_4$ | Physical Properties [ ] m.p. °C. |
|---|---|---|---|---|---|---|
| 624 | 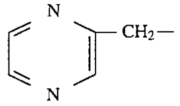 | H | $CH_3$ | CH | CN | |
| 625 | " | $CH_3$ | " | " | " | |
| 626 | 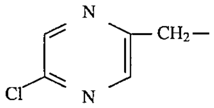 | H | " | " | " | |
| 627 | " | $CH_3$ | " | " | " | |
| 628 | 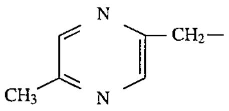 | H | " | " | " | |
| 629 | " | $CH_3$ | " | " | " | |
| 630 | 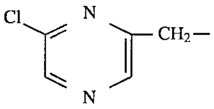 | H | " | " | " | |
| 631 | " | $CH_3$ | " | " | " | |
| 632 | 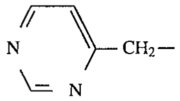 | H | " | " | " | |
| 633 | " | $CH_3$ | " | " | " | |

TABLE 1-continued
Structure Formula
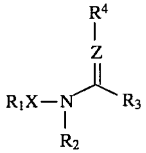
| Compound No. | $R_1X$ | $R_2$ | $R_3$ | Z | $R_4$ | Physical Properties [ ] m.p. °C. |
|---|---|---|---|---|---|---|
| 634 | 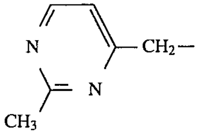 | H | " | " | " | |
| 635 | 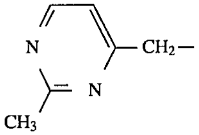 | $CH_3$ | $CH_3$ | CH | CN | |
| 636 | 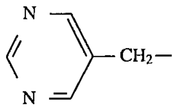 | H | " | " | " | |
| 637 | " | $CH_3$ | " | " | " | |
| 638 | 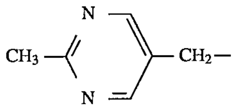 | H | " | " | " | |
| 639 | " | $CH_3$ | " | " | " | |
| 640 | 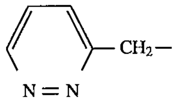 | H | " | " | " | |
| 641 | " | $CH_3$ | " | " | " | |

TABLE 1-continued
Structure Formula
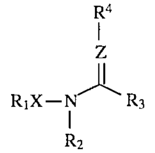
| Compound No. | $R_1X$ | $R_2$ | $R_3$ | Z | $R_4$ | Physical Properties [ ] m.p. °C. |
|---|---|---|---|---|---|---|
| 642 | 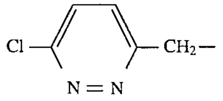 | H | " | " | " | |
| 643 | " | $CH_3$ | " | " | " | |
| 644 | 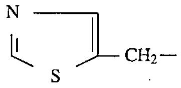 | H | $CH_3$ | CH | CN | |
| 645 | " | $CH_3$ | " | " | " | |
| 646 | 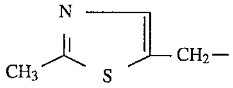 | H | " | " | " | |
| 647 | " | $CH_3$ | " | " | " | |
| 648 | 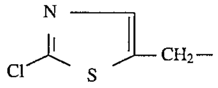 | H | " | " | " | |
| 649 | " | $CH_3$ | " | " | " | |
| 650 | " | " | $C_2H_5$ | " | " | |
| 651 | " | $C_2H_5$ | $CH_3$ | " | " | |
| 652 | 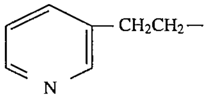 | H | $CH_3$ | CH | CN | |
| 653 | " | $CH_3$ | " | " | " | |

TABLE 1-continued
Structure Formula
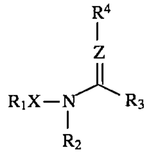
| Compound No. | $R_1X$ | $R_2$ | $R_3$ | Z | $R_4$ | Physical Properties [ ] m.p. °C. |
|---|---|---|---|---|---|---|
| 654 | 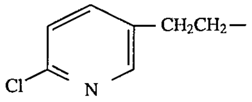 | H | " | " | " | |
| 655 | " | $CH_3$ | " | " | " | |
| 656 | 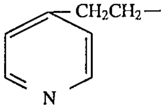 | H | " | " | " | |
| 657 | " | $CH_3$ | " | " | " | |
| 658 | 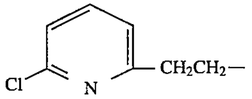 | H | " | " | " | |
| 659 | " | $CH_3$ | " | " | " | |
| 660 | 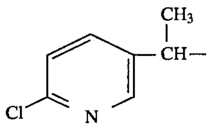 | H | " | " | " | |
| 661 | " | $CH_3$ | " | " | " | |
| 662 | 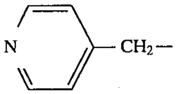 | H | " | " | " | |
| 663 | " | $CH_3$ | " | " | " | |

TABLE 1-continued
Structure Formula
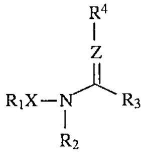
| Compound No. | $R_1X$ | $R_2$ | $R_3$ | Z | $R_4$ | Physical Properties [ ] m.p. °C. |
|---|---|---|---|---|---|---|
| 664 | 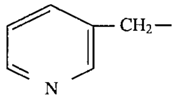 | H | H | CH | CN | |
| 665 | " | " | $CH_3$ | " | " | |
| 666 | " | " | $CH_2Cl$ | " | " | |
| 667 | " | " | $C_2H_5$ | " | " | |
| 668 | " | " | $C_3H_7$(i) | " | " | |
| 669 | " | " | $C_4H_9$(t) | " | " | |
| 670 | " | $CH_3$ | H | " | " | |
| 671 | " | " | $CH_3$ | " | " | |
| 672 | " | " | $CH_2Cl$ | " | " | |
| 673 | " | " | $C_2H_5$ | " | " | |
| 674 | " | " | 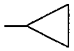 | " | " | |
| 675 | 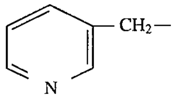 | $CH_3$ | $C_3H_7$(i) | CH | CN | |
| 676 | " | " | $C_4H_9$(t) | " | " | |
| 677 | " | $C_2H_5$ | H | " | " | |
| 678 | " | " | $CH_3$ | " | " | |
| 679 | " | " | $C_2H_5$ | " | " | |
| 680 | " | 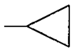 | H | " | " | |
| 681 | " | " | $CH_3$ | " | " | |
| 682 | " | " | $C_2H_5$ | " | " | |
| 683 | " | $COCH_3$ | H | " | " | |
| 684 | " | " | $CH_3$ | " | " | |
| 685 | " | " | $C_2H_5$ | " | " | |
| 686 | " | $SO_2CH_3$ | H | " | " | |

TABLE 1-continued
Structure Formula
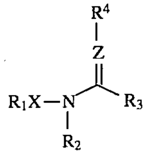
| Compound No. | $R_1X$ | $R_2$ | $R_3$ | Z | $R_4$ | Physical Properties [ ] m.p. °C. |
|---|---|---|---|---|---|---|
| 687 | 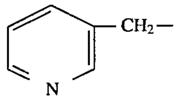 | $SO_2CH_3$ | $CH_3$ | CH | CN | |
| 688 | " | " | $C_2H_5$ | " | " | |
*1 $^1$H-NMR($CDCl_3$) δ; ppm 3.32 (s, 3H), 4.63 (s, 2H), 7.37 (d, 1H), 7.62 (dd, 1H), 8.37 (d, 1H)

Further, the following compound is described in U.S. Pat. No. 4,918,088, which has insecticidal activities.

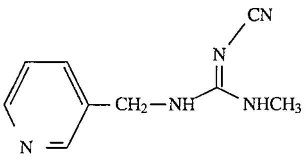

The compound however shows no insecticidal activity against lepidopterous insects and green rice leafhopper which are more serious pests on crops, though it shows some activity against cotton aphid.

The purpose of this invention is to provide agricultural chemicals which can be advantageously synthesized industrially, have certain effects and may be applied safely.

The compound of this invention has high insecticidal activity against both lepidopterous and hemipterous insects.

SUMMARY OF THE INVENTION

The present invention relates to a compound having the formula

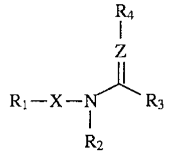

(I)

wherein $R_1$ represents an optionally substituted 5-6 membered aromatic hetero ring containing nitrogen atom, except a non-substituted 2-pyridyl;

X represents an optionally substituted $C_{1-3}$ alkylene or alkylidene;

$R_2$ represents a hydrogen, a carbamoyl, a mono or di $C_{1-5}$ alkyl carbamoyl, a thiocarbamoyl, a mono or di $C_1$ alkylthiocarbamoyl, a sulfamoyl, a mono or di $C_1$ alkylsulfamoyl, an optionally substituted $C_{1-5}$ alkyl, an optionally substituted $C_{2-5}$ alkenyl, an optionally substituted $C_{2-5}$ alkynyl, an optionally substituted $C_{3-8}$ cycloalkyl, an optionally substituted $C_{3-8}$ cycloalkenyl, an optionally substituted aryl or —Y—$R_5$;

Y represents O, $S(O)_n$, CO, CS or $CO_2$;

n represents 0,1 or 2;

$R_5$ represents a hydrogen, an optionally substituted $C_{1-5}$ alkyl, an optionally substituted $C_{2-5}$ alkenyl, an optionally substituted $C_{2-5}$ alkynyl, an optionally substituted $C_{3-8}$ cycloalkyl, an optionally substituted $C_{3-8}$ cycloalkenyl or an optionally substituted aryl;

$R_3$ represents a hydrogen, an optionally substituted $C_{1-5}$ alkyl, an optionally substituted $C_{2-5}$ alkenyl, an optionally substituted $C_{2-5}$ alkynyl, an optionally substituted $C_{3-8}$ cycloalkyl or an optionally substituted $C_{3-8}$ cycloalkenyl;

$R_4$ represents a cyano or a nitro; and Z represents CH or N; or its salt.

DESCRIPTION OF THE PREFERRED EMBODIMENTS

The compounds of this invention can be prepared in accordance with the following reaction schemes:

(1) Preparation Method 1:

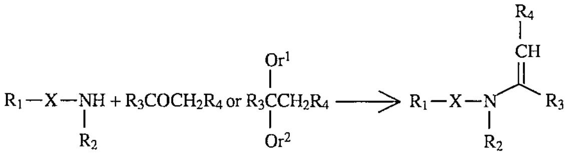

(II) (III) (III)' (I')

where $r^1$ and $r^2$ represent a $C_{1-5}$ alkyl; and $R_1$, $R_2$, $R_3$, $R_4$ and X are as defined above.

The reaction is carried out in an inactive organic solvent, preferably in an aromatic hydrocarbon solvent such as xylene, toluene or benzene, in the presence of acidic catalyst such as p-toluenesulfonic acid, if necessary, under reflux.

(2) Preparation method 2:

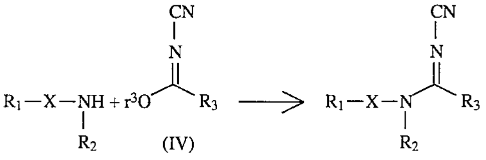

(II) (IV) (I")

where $r^3$ represents a $C_{1-5}$ alkyl:

and $R_1$, $R_2$, $R_3$ and X are as defined above. This reaction is carried out in an inactive organic solvent, preferably in an alcohol such as methanol, ethanol, between room temperature and the boiling point of the used solvent.

(3) Preparation Method 3:

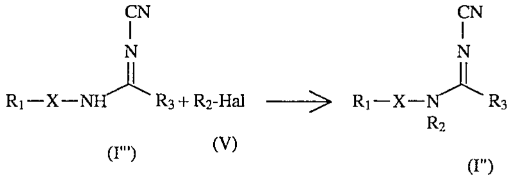

(I''') (V) (I")

where Hal represents a halogen; and $R_1$, $R_2$, $R_3$ and X are as defined above.

This reaction is carried out in an inactive organic solvent, preferably DMF, THF, benzene acetonitrile, acetone, methylethylketone, in the presence of acid accepter such as potassium carbonate, NaH, triethylamine, between room temparature and the boiling point of the used solvent.

(4) Preparation Method 4:

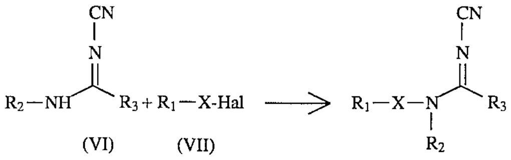

(VI) (VII) (I")

where $R_1$, $R_2$, $R_3$, X and Hal are as defined above. This reaction is carried out in the same manner as that of Preparation Method 3.

(5) Preparation Method 5:

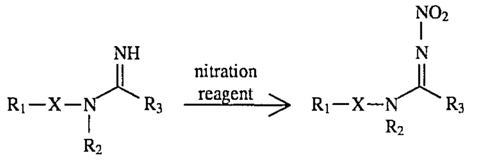

(VIII) (I''')

where $R_1$, $R_2$, $R_3$ and X are as defined above. This reaction is carried out in an inactive organic solvent, preferably acetonitrile, carbon tetrachloride, dichloroethane, in the presence of nitration reagent such as nitronium tetrafluoroborate, between −20° C. and the boiling point of the used solvent.

After the reaction is completed, an usual after-treatment gives the intended compound. The structure of the compounds of this invention was determined by such means as IR, NMR, MASS, etc. When $R_2$ is hydrogen in a compound of this invention, tautomers represented by

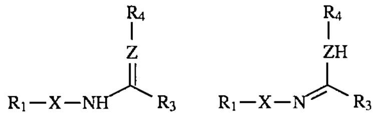

can exist.

The syn—aniti isomers, when Z represents N, and the cis-trans isomers, when Z represents CH, as represented by,

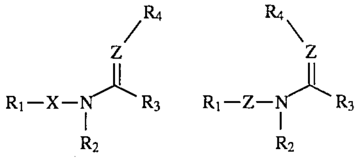

can also exist.

The ratio varies depending on e.g. conditions of instrumental analysis.

EXAMPLES

The following examples illustrate the present invention.

Example 1

2-(2-chloro-5-pyridylmethylamino)-1-nitro-1-butene:

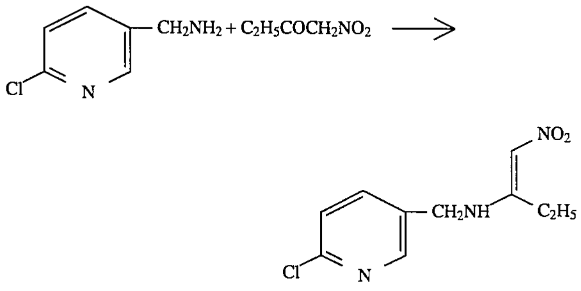

In 50 ml of toluene, 4.2 g of 2-chloro-5-pyridylmethylamine, 3.5 g of 1-nitro-2-butanone and 0.1 g of p-toluene sulfonic acid were mixed and the mixture was refluxed for 2 hours. The solvent was then distilled off and the residue was purified by column chromatography on silica gel to afford 4.1 g of compound No. 368. m.p. 95°–98° C.

Example 2

2-(2-chloro-5-pyridylmethylamino)-1-cyano-1-propene:

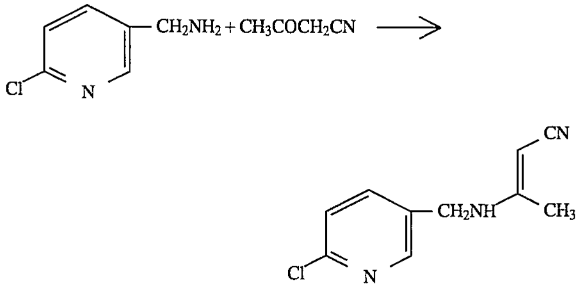

1.4 g of 2-chloro-5-pyridylmethylamine and 0.8 g of 1-cyano-2-propanone were mixed and the mixture was stirred at room temperature over night. The solvent was then distilled off and the residue was purified by column chromatography on silica gel to afford 1.7 g of compound No. 528. m.p. 95°–98° C.

Example 3

N-cyano-N'-(2-chloro-5-pyridylmethyl)-N'-methylacetamidine:

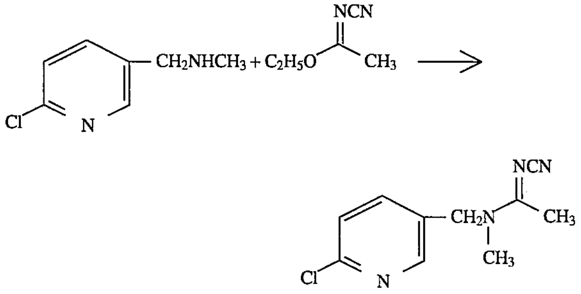

In 20 ml of ethanol, 1.6 g of N-methyl-2-cloro-5-pyridylmethylamine and 1.2 g of ethyl-N-cyanoacetamidine were mixed and the mixture was stirred at room temperature over night. The solvent was then distilled off and the residue was purified by column chromatography on silica gel to afford 1.8 g of compound No. 22. m.p. 101°–103° C.

Example 4

N-cyano-N'-(2-chloro-5-pyridylmethyl)-N'-ethylacetamidine:

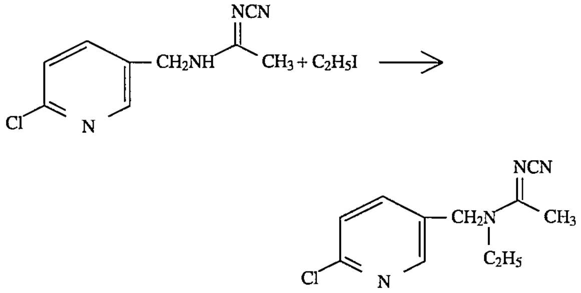

0.7 g of sodium hydride (purity 60%) was added to the solution of 3.0 g of N-cyano-N'-(2-chloro-5-pyridylmethyl)acetamidine in 20 ml of N.N-dimthylformamide at ice bath temperature. After stirring it at the same temperature for 1 hour, 2.7 g of ethyl iodide was added to the mixture, followed by stirring for 5 hours at room temperature. The reaction mixture was then poured into ice-water, extracted with ethyl acetate, dried over anhydrous magnesium sulfate and concentrated under reduced pressre. The residue obtained was purified by column chromatography on silica gel to afford 1.6 g of compound No. 51. m.p. 100°–101° C.

Example 5

N-cyano-N-(2-chloro-5-pyridylmethyl)-N'-methylacetamidine:

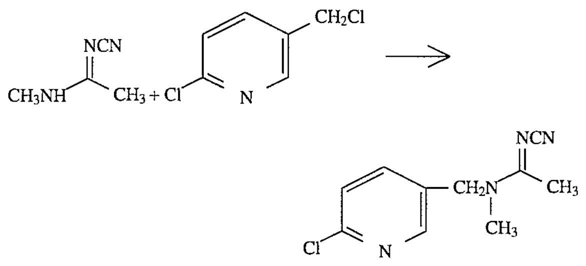

0.6 g of sodium hydride (purity 60%) was added to the solution of 1.3 g of N-cyano-N'-methylacetamidine in 20 ml of N,N-dimethylformamide at ice bath temperature. After stirring it at the same temperature for 1 hour, 2.2 g of 2-chloro-5-pyridylmethylchlride was added to the mixture, followed by stirring for 5 hours at room temperature. The reaction mixture was then poured into ice-water, extrated with ethyl acetate, dried over anhydrous magnesium sulfate and concentrated under reduced pressre. The residue obtained was purified by column chromatography on silica gel to afford 1.5 g of compound No. 22 m.p. 101–°103° C.

Reference Example

N-(2-chloro-5-pyridylmethyl)-N-methylacetamidine hydrochloride:

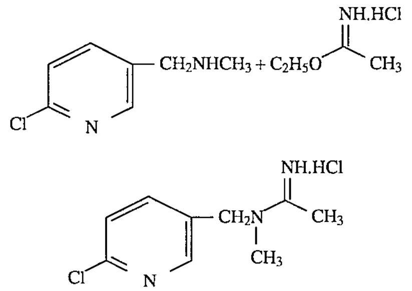

To 40 ml of ethanol was added 5.1 g of N-(2-chloro-5-pyridylmethyl)-N-Methylamine and then 4 g of ethyl acetimidate hydrochloride at 0° C. After stirring for an hour, the reaction mixture was allowed to warm to room temperature and stirred over night. The solvent was then distilled off. The obtained white residue was washed with diethyl ether to afford 7.3 g of the title compound m.p. 192–°197° C.

Example 6

N-(2-chloro-5-pyridylmethyl)-N-methyl-N'-nitroacetamidine:

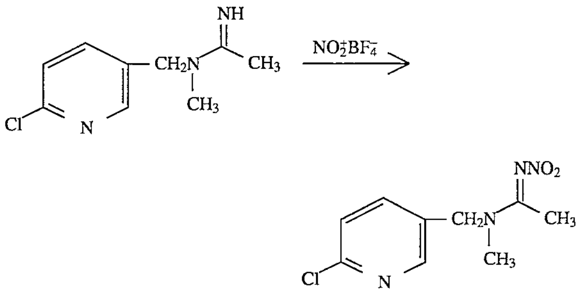

To a suspension of 1 g of N-(2-chloro-5-pyridylmethyl)-N-methylamidine hydrochloride in 10 ml of dry acetonitrile was added dropwise 0.7 g of DBU under nitrogen at room temperature. After stirring for 30 minutes, the solution was added dropwise to a suspension of 0.6 g of nitronium tetrafluoroborate in 5 ml of dry acetonitrile under nitrogen on cooling with ice-water and let stir for 4 hours. After which time, the mixture was poured into ice-water, then extracted several time with chloroform. The combined chloroform layer was dried over magnesium sulfate, filtered and distilled off. The crude oil was purified by column chromatgraphy on silica gel to afford 0,3 g of compound No. 236.

$N_D^{25}$1.5808

Typical examples of this invention including those described above are listed in Table 1.

TABLE 1
Structure Formula
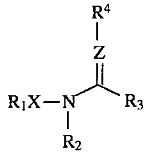
| Compound No. | $R_1X$ | $R_2$ | $R_3$ | Z | $R_4$ | Physical Properties [ ] m.p. °C. |
|---|---|---|---|---|---|---|
| 1 | 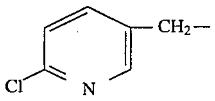 | H | H | N | CN | [123–126] |
| 2 | " | " | $CH_3$ | " | " | [141–143] |
| 3 | " | " | $CH_2Cl$ | " | " | [124–126] |
| 4 | " | " | $CH_2F$ | " | " | [151–152] |
| 5 | " | " | $CF_3$ | " | " | [112–114] |
| 6 | " | " | $C_2H_5$ | " | " | [120–122] |
| 7 | " | " | $C_3H_7(n)$ | " | " | [100–101] |
| 8 | " | " | 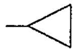 | " | " | [193.5–195] |
| 9 | " | " | $C_4H_9(t)$ | " | " | |
| 10 | " | " | $CH_2OCH_3$ | " | " | [128–128.5] |
| 11 | " | " | $CH_2SCH_3$ | " | " | [116–118] |
| 12 | 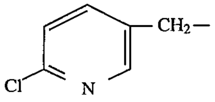 | " | $CH_2COOC_2H_5$ | N | CN | $n_D^{25.5}$ 1.5608 |
| 13 | " | " | $CH_2CH_2COOC_2H_5$ | " | " | |
| 14 | " | " | $CH_2NHCH_3$ | " | " | |
| 15 | " | " | $CH_2N(CH_3)_2$ | " | " | |
| 16 | " | " | $CH_2CH_2CH_2Cl$ | " | " | [114–115] |
| 17 | " | " | 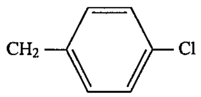 | " | " | [190–191] |
| 18 | " | " | $CH_2CN$ | " | " | [106–108] |
| 19 | " | " | $CH_2CH_2CN$ | " | " | |

TABLE 1-continued

Structure Formula

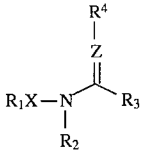

| Compound No. | $R_1X$ | $R_2$ | $R_3$ | Z | $R_4$ | Physical Properties [ ] m.p. °C. |
|---|---|---|---|---|---|---|
| 20 | " | " | 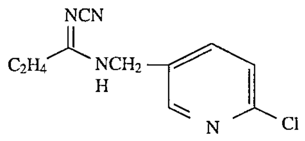 | " | " | [187–189] |
| 21 | " | $CH_3$ | H | " | " | $n_D^{25}$ 1.5918 |
| 22 | " | " | $CH_3$ | " | " | [101–103] |
| 23 | " | " | " | " | " | [161–162] HCl salt |
| 24 | " | " | $CH_2Cl$ | " | " | $n_D^{26.5}$ 1.5921 |
| 25 | " | " | $CH_2F$ | " | " | [79–80] |
| 26 | " | " | $CF_3$ | " | " | *1 |
| 27 | 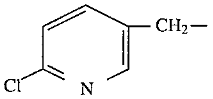 | $CH_3$ | $C_2H_5$ | N | CN | $n_D^{27}$ 1.5742 |
| 28 | " | " | $C_3H_7(n)$ | " | " | [97–100] |
| 29 | " | " | 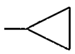 | " | " | $n_D^{24.5}$ 1.5829 |
| 30 | " | " | $C_4H_9(t)$ | " | " | |
| 31 | " | " | $CH_2OCH_3$ | " | " | $n_D^{24}$ 1.5803 |
| 32 | " | " | $CH_2SCH_3$ | " | " | $n_D^{24.5}$ 1.6070 |
| 33 | " | " | $CH_2COOC_2H_5$ | " | " | $n_D^{25.5}$ 1.5604 |
| 34 | " | " | $CH_2CH_2COOC_2H_5$ | " | " | $n_D^{24.5}$ 1.5605 |
| 35 | " | " | $CH_2NHCH_3$ | " | " | $n_D^{25}$ 1.5861 |
| 36 | " | " | $CH_2N(CH_3)_2$ | " | " | $n_D^{25}$ 1.5577 |
| 37 | " | " | $CH_2CH_2Cl$ | " | " | |
| 38 | " | " | $CH_2CH_2CH_2Cl$ | " | " | $n_D^{25.5}$ 1.5830 |
| 39 | " | " | 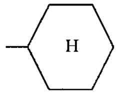 | " | " | |

TABLE 1-continued
Structure Formula
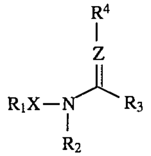
| Compound No. | $R_1X$ | $R_2$ | $R_3$ | Z | $R_4$ | Physical Properties [ ] m.p. °C. |
|---|---|---|---|---|---|---|
| 40 | " | " | 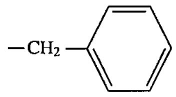 | " | " | |
| 41 | " | " | 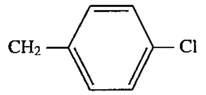 | " | " | $n_D^{25.5}$ 1.6040 |
| 42 | 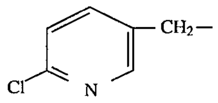 | $CH_3$ | $CH=CH_2$ | N | CN | |
| 43 | " | " | $CH_2CN$ | " | " | $n_D^{25}$ 1.5913 |
| 44 | " | " | $CH_2CH_2CN$ | " | " | [112–114] |
| 45 | " | " | 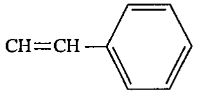 | " | " | |
| 46 | " | " | 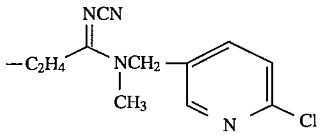 | " | " | [224–226] |
| 47 | " | $CHF_2$ | H | " | " | |
| 48 | " | " | $CH_3$ | " | " | $n_D^{24.5}$ 1.5423 |
| 49 | " | " | $C_2H_5$ | " | " | |
| 50 | " | $C_2H_5$ | H | " | " | [101–103] |
| 51 | " | " | $CH_3$ | " | " | [100–101] |
| 52 | " | " | $C_2H_5$ | " | " | |
| 53 | " | $C_3H_7(i)$ | H | " | " | [205–207] |
| 54 | " | " | $CH_3$ | " | " | |
| 55 | " | " | $C_2H_5$ | " | " | |

TABLE 1-continued
Structure Formula
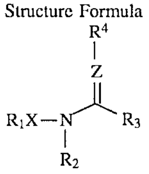
| Compound No. | $R_1X$ | $R_2$ | $R_3$ | Z | $R_4$ | Physical Properties [ ] m.p. °C. |
|---|---|---|---|---|---|---|
| 56 | " | 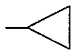 | H | " | " | |
| 57 | 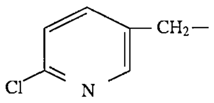 | 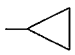 | $CH_3$ | N | CN | $n_D^{25}$ 1.5825 |
| 58 | " | " | $C_2H_5$ | " | " | |
| 59 | " | $CH_2OCH_3$ | H | " | " | |
| 60 | " | " | $CH_3$ | " | " | $n_D^{25.5}$ 1.5711 |
| 61 | " | $CH_2SCH_3$ | H | " | " | |
| 62 | " | " | $CH_3$ | " | " | $n_D^{25}$ 1.5828 |
| 63 | " | $CH_2COOC_2H_5$ | H | " | " | |
| 64 | " | " | $CH_3$ | " | " | $n_D^{25}$ 1.5475 |
| 65 | " | 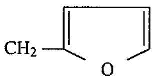 | H | " | " | |
| 66 | " | " | $CH_3$ | " | " | $n_D^{25.5}$ 1.5928 |
| 67 | " | 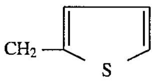 | H | " | " | |
| 68 | " | " | $CH_3$ | " | " | $n_D^{25.5}$ 1.6155 |
| 69 | " | 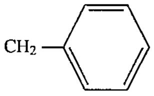 | H | " | " | |
| 70 | " | " | $CH_3$ | " | " | $n_D^{24.5}$ 1.6093 |
| 71 | " | 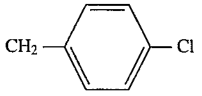 | H | " | " | |

TABLE 1-continued
Structure Formula
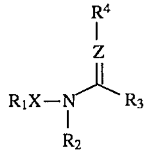
| Compound No. | $R_1X$ | $R_2$ | $R_3$ | Z | $R_4$ | Physical Properties [ ] m.p. °C. |
|---|---|---|---|---|---|---|
| 72 | 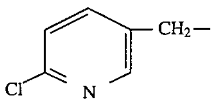 | 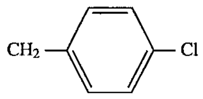 | $CH_3$ | N | CN | [112–114] |
| 73 | " | $CH_2CH=CH_2$ | H | " | " | $n_D^{25}$ 1.5841 |
| 74 | " | " | $CH_3$ | " | " | $n_D^{25}$ 1.5809 |
| 75 | " | $CH_2C\equiv CH$ | H | " | " | |
| 76 | " | " | $CH_3$ | " | " | $n_D^{25.5}$ 1.5730 |
| 77 | " | $CH_2CN$ | H | " | " | |
| 78 | " | " | $CH_3$ | " | " | [127–128] |
| 79 | " | 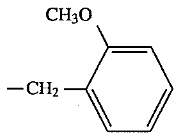 | H | " | " | |
| 80 | " | " | $CH_3$ | " | " | [124–127] |
| 81 | " | 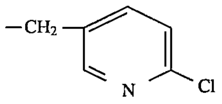 | H | " | " | |
| 82 | " | " | $CH_3$ | " | " | $n_D^{24.5}$ 1.6045 |
| 83 | " | 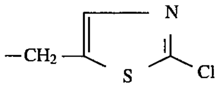 | H | " | " | |
| 84 | " | " | $CH_3$ | " | " | $n_D^{25.5}$ 1.6092 |
| 85 | " | 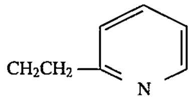 | H | " | " | |

TABLE 1-continued
Structure Formula
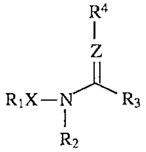
| Compound No. | $R_1X$ | $R_2$ | $R_3$ | Z | $R_4$ | Physical Properties [ ] m.p. °C. |
|---|---|---|---|---|---|---|
| 86 | 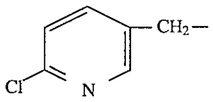 | 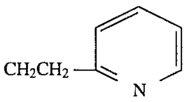 | $CH_3$ | N | CN | $n_D^{25.5}$ 1.5910 |
| 87 | " | 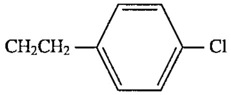 | H | " | " | |
| 88 | " | " | $CH_3$ | " | " | $n_D^{25.5}$ 1.6162 |
| 89 | " | 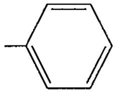 | H | " | " | |
| 90 | " | " | $CH_3$ | " | " | [115–117] |
| 91 | " | $OCH_3$ | H | " | " | |
| 92 | " | " | $CH_3$ | " | " | [110–112] |
| 93 | " | CHO | H | " | " | |
| 94 | " | " | $CH_3$ | " | " | |
| 95 | " | $COCH_3$ | H | " | " | $n_D^{25.5}$ 1.5475 |
| 96 | " | " | $CH_3$ | " | " | [84–86] |
| 97 | " | $SO_2CH_3$ | H | " | " | [160–163] |
| 98 | " | " | $CH_3$ | " | " | |
| 99 | " | 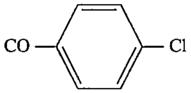 | H | " | " | |
| 100 | " | " | $CH_3$ | " | " | [112–114] |
| 101 | 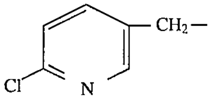 | $COOC_2H_5$ | H | N | CN | |

TABLE 1-continued
Structure Formula
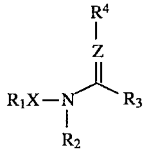
| Compound No. | $R_1X$ | $R_2$ | $R_3$ | Z | $R_4$ | Physical Properties [ ] m.p. °C. |
|---|---|---|---|---|---|---|
| 102 | " | " | $CH_3$ | " | " | $n_D^{25}$ 1.5540 |
| 103 | " | $CONH_2$ | H | " | " | |
| 104 | " | " | $CH_3$ | " | " | |
| 105 | " | 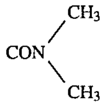 | H | " | " | |
| 106 | " | " | $CH_3$ | " | " | [89–91] |
| 107 | " | $CONHCH_3$ | H | " | " | |
| 108 | " | " | $CH_3$ | " | " | |
| 109 | " | $CSNHCH_3$ | H | " | " | |
| 110 | " | " | $CH_3$ | " | " | |
| 111 | 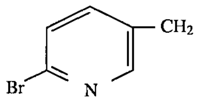 | H | $CH_3$ | " | " | |
| 112 | " | $CH_3$ | " | " | " | |
| 113 | 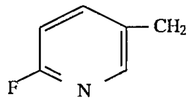 | H | " | " | " | |
| 114 | " | $CH_3$ | " | " | " | |
| 115 | 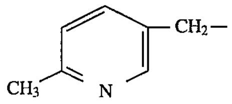 | H | " | " | " | [83–85] |

TABLE 1-continued
Structure Formula
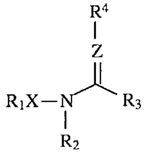
| Compound No. | $R_1X$ | $R_2$ | $R_3$ | Z | $R_4$ | Physical Properties [ ] m.p. °C. |
|---|---|---|---|---|---|---|
| 116 | 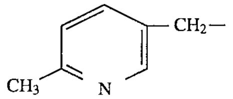 | $CH_3$ | $CH_3$ | N | CN | [76-78] |
| 117 | 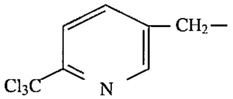 | H | " | " | " | |
| 118 | " | $CH_3$ | " | " | " | [145-147] |
| 119 | 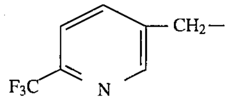 | H | " | " | " | |
| 120 | " | $CH_3$ | " | " | " | $n_D^{25}$ 1.5202 |
| 121 | 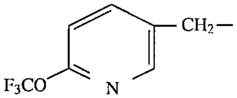 | H | " | " | " | |
| 122 | " | $CH_3$ | " | " | " | |
| 123 | 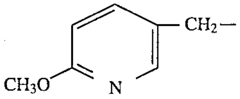 | H | " | " | " | |
| 124 | " | $CH_3$ | " | " | " | $n_D^{25.5}$ 1.5580 |
| 125 | 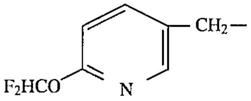 | H | " | " | " | |

TABLE 1-continued
Structure Formula
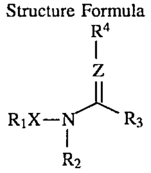
| Compound No. | $R_1X$ | $R_2$ | $R_3$ | Z | $R_4$ | Physical Properties [ ] m.p. °C. |
|---|---|---|---|---|---|---|
| 126 | " | $CH_3$ | " | " | " | |
| 127 | 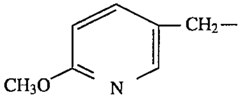 | H | " | " | " | |
| 128 | " | $CH_3$ | " | " | " | |
| 129 | 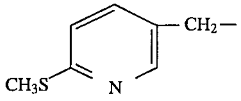 | H | " | " | " | [162–163] |
| 130 | " | $CH_3$ | " | " | " | [105–107] |
| 131 | 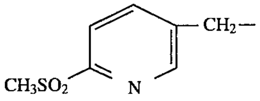 | H | $CH_3$ | N | CN | |
| 132 | " | $CH_3$ | " | " | " | [138–139] |
| 133 | 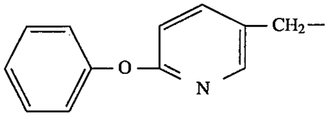 | H | " | " | " | |
| 134 | " | $CH_3$ | " | " | " | $n_D^{25}$ 1.5841 |
| 135 | 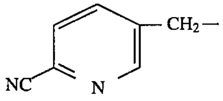 | H | " | " | " | |
| 136 | " | $CH_3$ | " | " | " | [107–109] |

TABLE 1-continued
Structure Formula
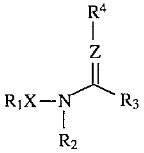
| Compound No. | $R_1X$ | $R_2$ | $R_3$ | Z | $R_4$ | Physical Properties [ ] m.p. °C. |
|---|---|---|---|---|---|---|
| 137 | 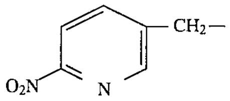 | H | " | " | " | |
| 138 | " | $CH_3$ | " | " | " | |
| 139 | 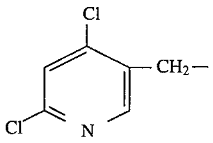 | H | " | " | " | |
| 140 | " | $CH_3$ | " | " | " | |
| 141 | 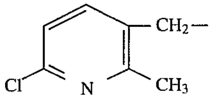 | H | " | " | " | |
| 142 | " | $CH_3$ | " | " | " | |
| 143 | 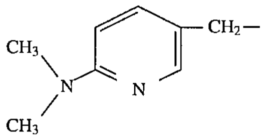 | H | " | " | " | [122–124] |
| 144 | " | $CH_3$ | " | " | " | [110–113] |
| 145 | 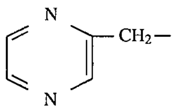 | H | $CH_3$ | N | CN | [66–68] |
| 146 | " | $CH_3$ | " | " | " | $n_D^{24.5}$ 1.5790 |

TABLE 1-continued
Structure Formula
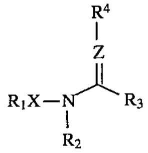
| Compound No. | $R_1X$ | $R_2$ | $R_3$ | Z | $R_4$ | Physical Properties [ ] m.p. °C. |
|---|---|---|---|---|---|---|
| 147 | 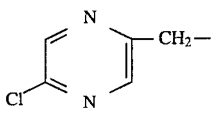 | H | " | " | " | |
| 148 | " | $CH_3$ | " | " | " | [94–96] |
| 149 | 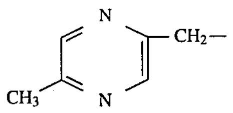 | H | " | " | " | [130–132] |
| 150 | " | $CH_3$ | " | " | " | $n_D^{25}$ 1.5612 |
| 151 | 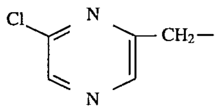 | H | " | " | " | [96–99] |
| 152 | " | $CH_3$ | " | " | " | $n_D^{25.5}$ 1.5800 |
| 153 | 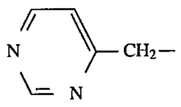 | H | " | " | " | |
| 154 | " | $CH_3$ | " | " | " | |
| 155 | 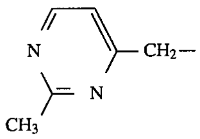 | H | " | " | " | |

TABLE 1-continued
Structure Formula
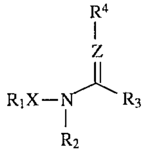
| Compound No. | $R_1X$ | $R_2$ | $R_3$ | Z | $R_4$ | Physical Properties [ ] m.p. °C. |
|---|---|---|---|---|---|---|
| 156 | 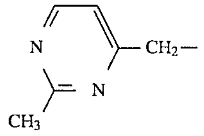 | $CH_3$ | $CH_3$ | N | CN | |
| 157 | 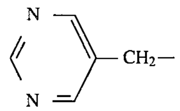 | H | " | " | " | |
| 158 | " | $CH_3$ | " | " | " | |
| 159 | 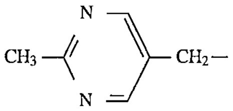 | H | " | " | " | |
| 160 | " | $CH_3$ | " | " | " | |
| 161 | 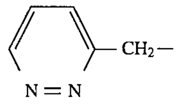 | H | " | " | " | |
| 162 | " | $CH_3$ | " | " | " | |
| 163 | 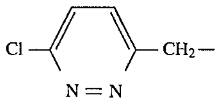 | H | " | " | " | [115-117] |
| 164 | " | $CH_3$ | " | " | " | $n_D^{23}$ 1.5717 |

TABLE 1-continued
Structure Formula
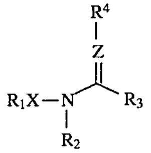
| Compound No. | $R_1X$ | $R_2$ | $R_3$ | Z | $R_4$ | Physical Properties [ ] m.p. °C. |
|---|---|---|---|---|---|---|
| 165 | 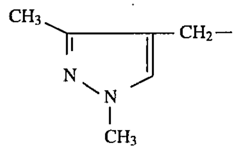 | H | " | " | " | [104–106] |
| 166 | " | $CH_3$ | " | " | " | |
| 167 | 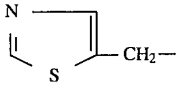 | H | $CH_3$ | N | CN | |
| 168 | " | $CH_3$ | " | " | " | |
| 169 | 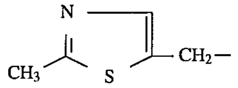 | H | " | " | " | [112–114] |
| 170 | " | $CH_3$ | " | " | " | $n_D^{25}$ 1.5413 |
| 171 | 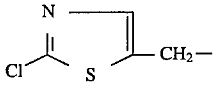 | H | " | " | " | [122–124] |
| 172 | " | $CH_3$ | " | " | " | [143–144] |
| 173 | " | " | $C_2H_5$ | " | " | $n_D^{25}$ 1.5575 |
| 174 | " | $C_2H_5$ | $CH_3$ | " | " | [63–70] |
| 175 | 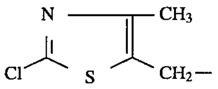 | H | " | " | " | [149–151] |
| 176 | " | $CH_3$ | " | " | " | |

TABLE 1-continued
Structure Formula
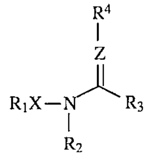
| Compound No. | $R_1X$ | $R_2$ | $R_3$ | Z | $R_4$ | Physical Properties [ ] m.p. °C. |
|---|---|---|---|---|---|---|
| 177 | 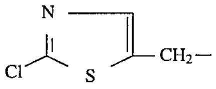 | H | H | " | " | [179-183] |
| 178 | " | $CH_3$ | " | " | " | $n_D^{25}$ 1.5952 |
| 179 | 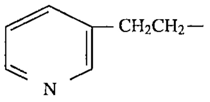 | H | $CH_3$ | N | CN | |
| 180 | " | $CH_3$ | " | " | " | |
| 181 | 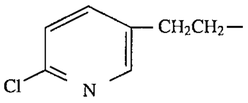 | H | " | " | " | |
| 182 | " | $CH_3$ | " | " | " | |
| 183 | 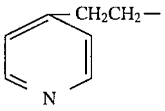 | H | " | " | " | |
| 184 | " | $CH_3$ | " | " | " | |
| 185 | 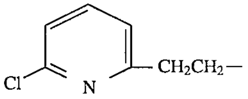 | H | " | " | " | |
| 186 | " | $CH_3$ | " | " | " | |

TABLE 1-continued
Structure Formula
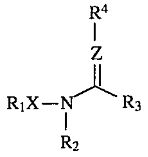
| Compound No. | $R_1X$ | $R_2$ | $R_3$ | Z | $R_4$ | Physical Properties [ ] m.p. °C. |
|---|---|---|---|---|---|---|
| 187 | 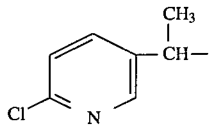 | H | " | " | " | |
| 188 | " | $CH_3$ | " | " | " | [106-109] |
| 189 | 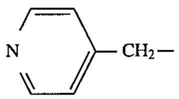 | H | $CH_3$ | " | " | [90-92] |
| 190 | 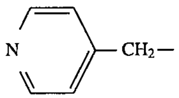 | $CH_3$ | $CH_3$ | N | CN | [102-103] |
| 191 | 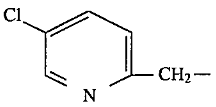 | H | " | " | " | |
| 192 | " | $CH_3$ | " | " | " | |
| 193 | 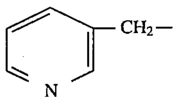 | H | H | " | " | |
| 194 | " | " | $CH_3$ | " | " | [127-129] |
| 195 | " | " | $CH_2Cl$ | " | " | |
| 196 | " | " | $CH_2F$ | " | " | |
| 197 | " | " | $C_2H_5$ | " | " | |
| 198 | " | " | 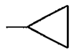 | " | " | |

TABLE 1-continued

Structure Formula

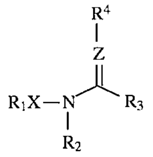

| Compound No. | $R_1X$ | $R_2$ | $R_3$ | Z | $R_4$ | Physical Properties [ ] m.p. °C. |
|---|---|---|---|---|---|---|
| 199 | " | " | $CH_2SCH_3$ | " | " | |
| 200 | " | " | $CH_2OCH_3$ | " | " | |
| 201 | 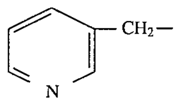 | H | $C_3H_7$(n) | N | CN | $n_D^{25.5}$ 1.5528 |
| 202 | " | $CH_3$ | H | " | " | |
| 203 | " | " | $CH_3$ | " | " | $n_D^{25.5}$ 1.5798 |
| 204 | " | " | $CH_2Cl$ | " | " | |
| 205 | " | " | $CH_2F$ | " | " | |
| 206 | " | H | $C_2H_5$ | " | " | $n_D^{25.5}$ 1.5657 |
| 207 | " | " | 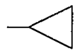 | " | " | |
| 208 | " | " | $CH_2SCH_3$ | " | " | |
| 209 | " | " | $CH_2OCH_3$ | " | " | |
| 210 | " | " | $C_3H_7$(i) | " | " | |
| 211 | " | " | $C_4H_9$(t) | " | " | |
| 212 | 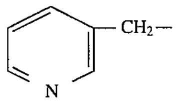 | $C_2H_5$ | H | N | CN | |
| 213 | " | " | $CH_3$ | " | " | $n_D^{24.5}$ 1.5665 |
| 214 | " | " | $CH_2Cl$ | " | " | |
| 215 | " | " | $C_2H_5$ | " | " | |
| 216 | " | $C_3H_7$(i) | H | " | " | |
| 217 | " | " | $CH_3$ | " | " | |
| 218 | " | " | $C_2H_5$ | " | " | |
| 219 | " | $COCH_3$ | H | " | " | |
| 220 | " | " | $CH_3$ | " | " | |
| 221 | " | $SO_2CH_3$ | H | " | " | |
| 222 | " | " | $CH_3$ | " | " | |

TABLE 1-continued
Structure Formula
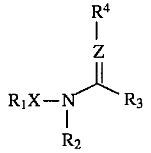
| Compound No. | $R_1X$ | $R_2$ | $R_3$ | Z | $R_4$ | Physical Properties [ ] m.p. °C. |
|---|---|---|---|---|---|---|
| 223 | 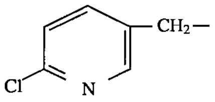 | H | H | N | $NO_2$ | |
| 224 | " | " | $CH_3$ | " | " | |
| 225 | " | " | $CH_2Cl$ | " | " | |
| 226 | " | " | $CH_2F$ | " | " | |
| 227 | " | " | $C_2H_5$ | " | " | |
| 228 | " | " | 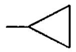 | " | " | |
| 229 | " | " | $CH_2SCH_3$ | " | " | |
| 230 | " | " | $CH_2OCH_3$ | " | " | |
| 231 | " | " | $C_3H_7(i)$ | " | " | |
| 232 | " | " | $C_4H_9(t)$ | " | " | |
| 233 | " | " | $CH{=}CH_2$ | " | " | |
| 234 | " | " | 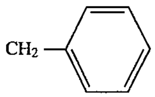 | " | " | |
| 235 | 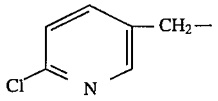 | $CH_3$ | H | N | $NO_2$ | |
| 236 | " | " | $CH_3$ | " | " | $n_D^{25}$ 1.5808 |
| 237 | " | " | $CH_2Cl$ | " | " | |
| 238 | " | " | $CH_2F$ | " | " | |
| 239 | " | " | $C_2H_5$ | " | " | |
| 240 | " | " | 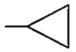 | " | " | |
| 241 | " | " | $CH_2SCH_3$ | " | " | |
| 242 | " | " | $CH_2OCH_3$ | " | " | |

TABLE 1-continued
Structure Formula
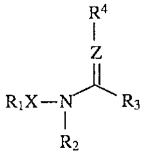
| Compound No. | $R_1X$ | $R_2$ | $R_3$ | Z | $R_4$ | Physical Properties [ ] m.p. °C. |
|---|---|---|---|---|---|---|
| 243 | " | " | $C_3H_7(n)$ | " | " | |
| 244 | " | " | $C_4H_9(t)$ | " | " | |
| 245 | " | " | $CH=CH_2$ | " | " | |
| 246 | " | " | 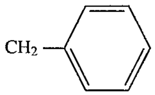 | " | " | |
| 247 | 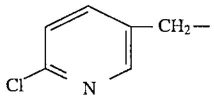 | $C_2H_5$ | H | N | $NO_2$ | |
| 248 | " | " | $CH_3$ | " | " | |
| 249 | " | " | $C_2H_5$ | " | " | |
| 250 | " | $C_3H_7(i)$ | H | " | " | |
| 251 | " | " | $CH_3$ | " | " | |
| 252 | " | " | $C_2H_5$ | " | " | |
| 253 | " | 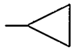 | H | " | " | |
| 254 | " | " | $CH_3$ | " | " | |
| 255 | " | " | $C_2H_5$ | " | " | |
| 256 | " | $COCH_3$ | H | " | " | |
| 257 | " | " | $CH_3$ | " | " | |
| 258 | " | $SO_2CH_3$ | H | " | " | |
| 259 | " | " | $CH_3$ | " | " | |
| 260 | 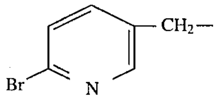 | H | $CH_3$ | N | $NO_2$ | |
| 261 | " | $CH_3$ | " | " | " | |

TABLE 1-continued
Structure Formula
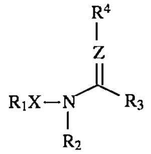
| Compound No. | $R_1X$ | $R_2$ | $R_3$ | Z | $R_4$ | Physical Properties [ ] m.p. °C. |
|---|---|---|---|---|---|---|
| 262 | 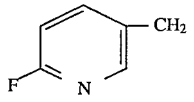 | H | " | " | " | |
| 263 | " | $CH_3$ | " | " | " | |
| 264 | 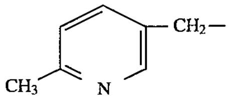 | H | " | " | " | |
| 265 | " | $CH_3$ | " | " | " | |
| 266 | 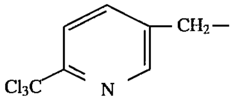 | H | " | " | " | |
| 267 | " | $CH_3$ | " | " | " | |
| 268 | 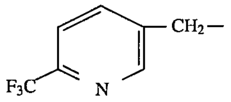 | H | " | " | " | |
| 269 | " | $CH_3$ | " | " | " | |
| 270 | 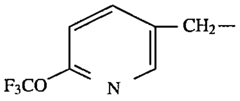 | H | " | " | " | |
| 271 | " | $CH_3$ | " | " | " | |

TABLE 1-continued
Structure Formula
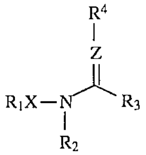
| Compound No. | $R_1X$ | $R_2$ | $R_3$ | Z | $R_4$ | Physical Properties [ ] m.p. °C. |
|---|---|---|---|---|---|---|
| 272 | 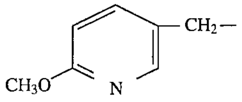 | H | $CH_3$ | N | $NO_2$ | |
| 273 | " | $CH_3$ | " | " | " | |
| 274 | 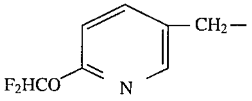 | H | " | " | " | |
| 275 | " | $CH_3$ | " | " | " | |
| 276 | 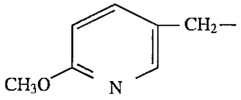 | H | " | " | " | |
| 277 | " | $CH_3$ | " | " | " | |
| 278 | 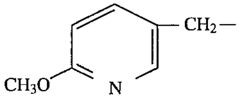 | H | " | " | " | |
| 279 | " | $CH_3$ | " | " | " | |
| 280 | 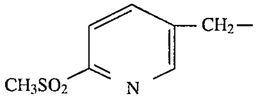 | H | " | " | " | |
| 281 | " | $CH_3$ | " | " | " | |

TABLE 1-continued
Structure Formula
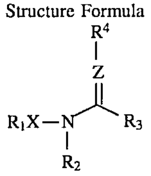
| Compound No. | $R_1X$ | $R_2$ | $R_3$ | Z | $R_4$ | Physical Properties [ ] m.p. °C. |
|---|---|---|---|---|---|---|
| 282 | 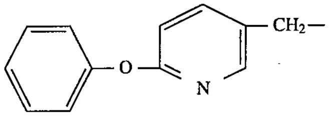 | H | " | " | " | |
| 283 | " | $CH_3$ | " | " | " | |
| 284 | 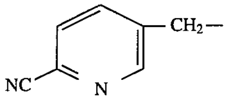 | H | $CH_3$ | N | $NO_2$ | |
| 285 | " | $CH_3$ | " | " | " | |
| 286 | 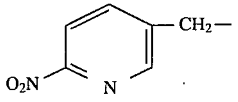 | H | " | " | " | |
| 287 | " | $CH_3$ | " | " | " | |
| 288 | 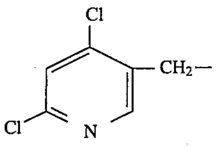 | H | " | " | " | |
| 289 | " | $CH_3$ | " | " | " | |
| 290 | 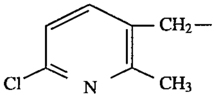 | H | " | " | " | |
| 291 | " | $CH_3$ | " | " | " | |

TABLE 1-continued
Structure Formula
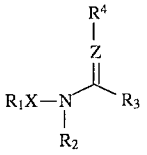
| Compound No. | $R_1X$ | $R_2$ | $R_3$ | Z | $R_4$ | Physical Properties [ ] m.p. °C. |
|---|---|---|---|---|---|---|
| 292 | 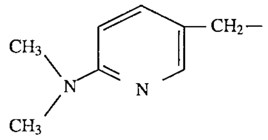 | H | " | " | " | |
| 293 | " | $CH_3$ | " | " | " | |
| 294 | 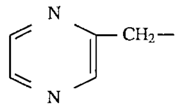 | H | $CH_3$ | N | $NO_2$ | |
| 295 | " | $CH_3$ | " | " | " | |
| 296 | 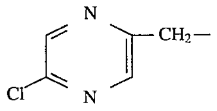 | H | " | " | " | |
| 297 | " | $CH_3$ | " | " | " | |
| 298 | 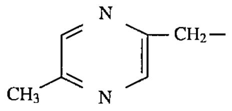 | H | " | " | " | |
| 299 | " | $CH_3$ | " | " | " | |
| 300 | 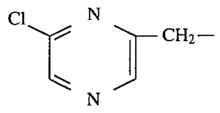 | H | " | " | " | |
| 301 | " | $CH_3$ | " | " | " | |

TABLE 1-continued
Structure Formula
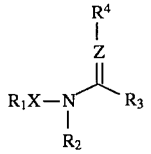
| Compound No. | $R_1X$ | $R_2$ | $R_3$ | Z | $R_4$ | Physical Properties [ ] m.p. °C. |
|---|---|---|---|---|---|---|
| 302 | 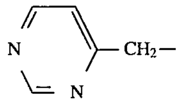 | H | " | " | " | |
| 303 | " | $CH_3$ | " | " | " | |
| 304 | 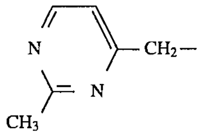 | H | " | " | " | |
| 305 | 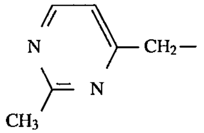 | $CH_3$ | $CH_3$ | N | $NO_2$ | |
| 306 | 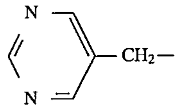 | H | " | " | " | |
| 307 | " | $CH_3$ | " | " | " | |
| 308 | 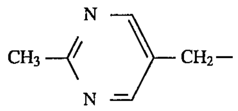 | H | " | " | " | |
| 309 | " | $CH_3$ | " | " | " | |

TABLE 1-continued
Structure Formula
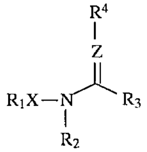
| Compound No. | $R_1X$ | $R_2$ | $R_3$ | Z | $R_4$ | Physical Properties [ ] m.p. °C. |
|---|---|---|---|---|---|---|
| 310 | 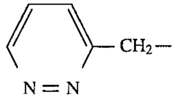 | H | " | " | " | |
| 311 | " | $CH_3$ | " | " | " | |
| 312 | 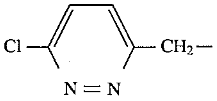 | H | " | " | " | |
| 313 | " | $CH_3$ | " | " | " | |
| 314 | 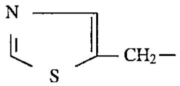 | H | $CH_3$ | N | $NO_2$ | |
| 315 | " | $CH_3$ | " | " | " | |
| 316 | 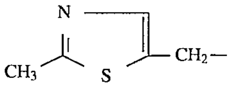 | H | " | " | " | |
| 317 | " | $CH_3$ | " | " | " | |
| 318 | 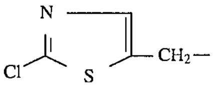 | H | " | " | " | |
| 319 | " | $CH_3$ | " | " | " | |
| 320 | " | " | $C_2H_5$ | " | " | |
| 321 | " | $C_2H_5$ | $CH_3$ | " | " | |
| 322 | 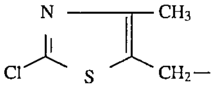 | H | " | " | " | |

TABLE 1-continued
Structure Formula
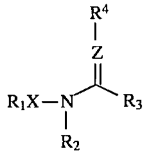
| Compound No. | $R_1X$ | $R_2$ | $R_3$ | Z | $R_4$ | Physical Properties [ ] m.p. °C. |
|---|---|---|---|---|---|---|
| 323 | " | $CH_3$ | " | " | " | |
| 324 | 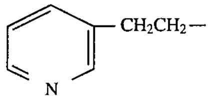 | H | $CH_3$ | N | $NO_2$ | |
| 325 | " | $CH_3$ | " | " | " | |
| 326 | 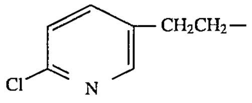 | H | " | " | " | |
| 327 | " | $CH_3$ | " | " | " | |
| 328 | 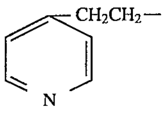 | H | " | " | " | |
| 329 | " | $CH_3$ | " | " | " | |
| 330 | 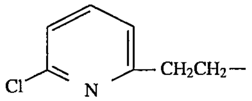 | H | " | " | " | |
| 331 | " | $CH_3$ | " | " | " | |
| 332 | 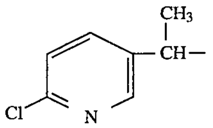 | H | " | " | " | |
| 333 | " | $CH_3$ | " | " | " | |

TABLE 1-continued
Structure Formula
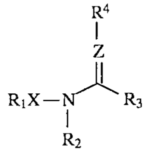
| Compound No. | $R_1X$ | $R_2$ | $R_3$ | Z | $R_4$ | Physical Properties [ ] m.p. °C. |
|---|---|---|---|---|---|---|
| 334 | 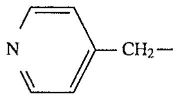 | H | " | " | " | |
| 335 | " | $CH_3$ | " | " | " | |
| 336 | 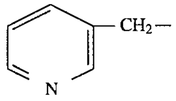 | H | H | N | $NO_2$ | |
| 337 | " | " | $CH_3$ | " | " | |
| 338 | " | " | $C_2H_5$ | " | " | |
| 339 | " | " | $CH_2Cl$ | " | " | |
| 340 | " | " | $CH_2F$ | " | " | |
| 341 | " | " | 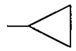 | " | " | |
| 342 | " | " | $CH_2SCH_3$ | " | " | |
| 343 | " | " | $CH_2OCH_3$ | " | " | |
| 344 | 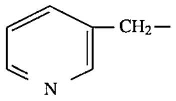 | $CH_3$ | H | N | $NO_2$ | |
| 345 | " | " | $CH_3$ | " | " | |
| 346 | " | " | $CH_2Cl$ | " | " | |
| 347 | " | " | $CH_2F$ | " | " | |
| 348 | " | " | $C_2H_5$ | " | " | |
| 349 | " | " | 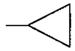 | " | " | |
| 350 | " | " | $CH_2SCH_3$ | " | " | |
| 351 | " | " | $CH_2OCH_3$ | " | " | |

TABLE 1-continued

Structure Formula

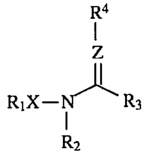

| Compound No. | $R_1X$ | $R_2$ | $R_3$ | Z | $R_4$ | Physical Properties [ ] m.p. °C. |
|---|---|---|---|---|---|---|
| 352 | " | " | $C_3H_7$(i) | " | " | |
| 353 | " | " | $C_4H_9$(t) | " | " | |
| 354 | 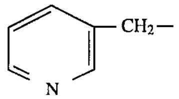 | $C_2H_5$ | H | N | $NO_2$ | |
| 355 | " | " | $CH_3$ | " | " | |
| 356 | " | " | $CH_2Cl$ | " | " | |
| 357 | " | " | $C_2H_5$ | " | " | |
| 358 | " | $C_3H_7$(i) | H | " | " | |
| 359 | " | " | $CH_3$ | " | " | |
| 360 | " | " | $C_2H_5$ | " | " | |
| 361 | " | $COCH_3$ | H | " | " | |
| 362 | " | " | $CH_3$ | " | " | |
| 363 | " | $SO_2CH_3$ | H | " | " | |
| 364 | " | " | $CH_3$ | " | " | |
| 365 | 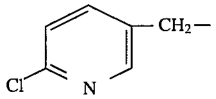 | H | H | CH | $NO_2$ | [116–118] |
| 366 | " | " | $CH_3$ | " | " | [133–135] |
| 367 | " | " | $CH_2Cl$ | " | " | |
| 368 | " | " | $C_2H_5$ | " | " | [95–98] |
| 369 | " | " | $C_3H_7$(i) | " | " | [150–152] |
| 370 | " | " | $C_4H_7$(t) | " | " | |
| 371 | " | " | $CH=CH_2$ | " | " | |
| 372 | " | " | $CH=CHCH_3$ | " | " | |
| 373 | " | " | $CH_2CN$ | " | " | |
| 374 | " | " | $CH_2NO_2$ | " | " | |
| 375 | " | " | $CH_2COOC_2H_5$ | " | " | |
| 376 | 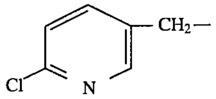 | H | 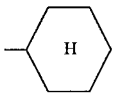 | CH | $NO_2$ | |

TABLE 1-continued
Structure Formula
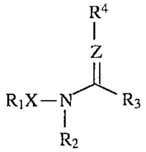
| Compound No. | $R_1X$ | $R_2$ | $R_3$ | Z | $R_4$ | Physical Properties [ ] m.p. °C. |
|---|---|---|---|---|---|---|
| 377 | " | " | 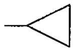 | " | " | |
| 378 | " | " | 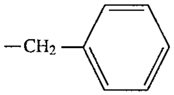 | " | " | |
| 379 | " | " | 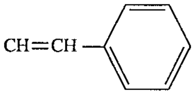 | " | " | |
| 380 | " | $CH_3$ | H | " | " | |
| 381 | " | " | $CH_3$ | " | " | [79-82] |
| 382 | " | " | $CH_2Cl$ | " | " | |
| 383 | " | " | $C_2H_5$ | " | " | [101-104] |
| 384 | " | " | $C_3H_7(i)$ | " | " | |
| 385 | " | " | $C_4H_7(t)$ | " | " | |
| 386 | " | " | $CH=CH_2$ | " | " | |
| 387 | " | " | $CH=CHCH_3$ | " | " | |
| 388 | 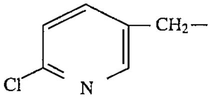 | $CH_3$ | $CH_2CN$ | CH | $NO_2$ | |
| 389 | " | " | $CH_2NO_2$ | " | " | |
| 390 | " | " | $CH_2COOC_2H_5$ | " | " | |
| 391 | " | " | 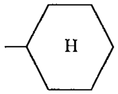 | " | " | |
| 392 | " | " | 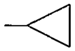 | " | " | |

TABLE 1-continued
Structure Formula
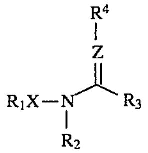
| Compound No. | $R_1X$ | $R_2$ | $R_3$ | Z | $R_4$ | Physical Properties [ ] m.p. °C. |
|---|---|---|---|---|---|---|
| 393 | " | " | 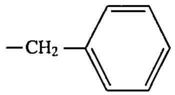 | " | " | |
| 394 | " | " | 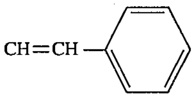 | " | " | |
| 395 | " | $C_2H_5$ | H | " | " | |
| 396 | " | " | $CH_3$ | " | " | |
| 397 | " | " | $C_2H_5$ | " | " | |
| 398 | " | $C_3H_7$(i) | H | " | " | |
| 399 | " | " | $CH_3$ | " | " | |
| 400 | 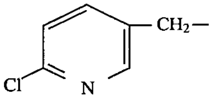 | $C_3H_7$(i) | $C_2H_5$ | CH | $NO_2$ | |
| 401 | " | 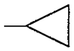 | H | " | " | |
| 402 | " | " | $CH_3$ | " | " | |
| 403 | " | " | $C_2H_5$ | " | " | |
| 404 | " | $CH_2CH{=}CH_2$ | H | " | " | |
| 405 | " | " | $CH_3$ | " | " | |
| 406 | " | " | $C_2H_5$ | " | " | |
| 407 | " | 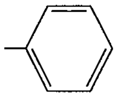 | H | " | " | |
| 408 | " | " | $CH_3$ | " | " | |
| 409 | " | " | $C_2H_5$ | " | " | |
| 410 | " | CHO | H | " | " | |
| 411 | " | " | $CH_3$ | " | " | |

TABLE 1-continued
Structure Formula
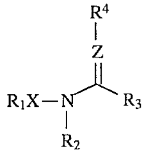
| Compound No. | $R_1X$ | $R_2$ | $R_3$ | Z | $R_4$ | Physical Properties [ ] m.p. °C. |
|---|---|---|---|---|---|---|
| 412 | 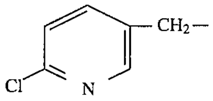 | CHO | $C_2H_5$ | CH | $NO_2$ | |
| 413 | " | $COCH_3$ | H | " | " | |
| 414 | " | " | $CH_3$ | " | " | |
| 415 | " | " | $C_2H_5$ | " | " | |
| 416 | " | $SO_2CH_3$ | H | " | " | |
| 417 | " | " | $CH_3$ | " | " | |
| 418 | " | " | $C_2H_5$ | " | " | |
| 419 | " | $COOC_2H_5$ | H | " | " | |
| 420 | " | " | $CH_3$ | " | " | |
| 421 | " | " | $C_2H_5$ | " | " | |
| 422 | " | $OC_2H_5$ | H | " | " | |
| 423 | " | " | $CH_3$ | " | " | |
| 424 | " | " | $C_2H_5$ | " | " | |
| 425 | " | $CH_2C{=}CH$ | H | " | " | |
| 426 | " | " | $CH_3$ | " | " | |
| 427 | " | " | $C_2H_5$ | " | " | |
| 428 | 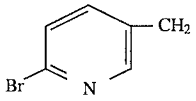 | H | $CH_3$ | CH | $NO_2$ | |
| 429 | " | $CH_3$ | " | " | " | |
| 430 | 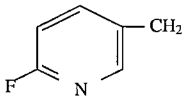 | H | " | " | " | |
| 431 | " | $CH_3$ | " | " | " | |
| 432 | 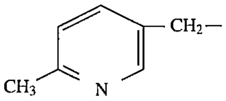 | H | " | " | " | |

TABLE 1-continued
Structure Formula
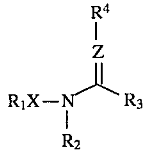
| Compound No. | $R_1X$ | $R_2$ | $R_3$ | Z | $R_4$ | Physical Properties [ ] m.p. °C. |
|---|---|---|---|---|---|---|
| 433 | " | $CH_3$ | " | " | " | |
| 434 | 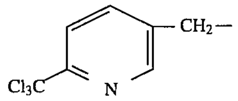 | H | " | " | " | |
| 435 | " | $CH_3$ | " | " | " | |
| 436 | 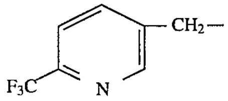 | H | " | " | " | |
| 437 | " | $CH_3$ | " | " | " | |
| 438 | 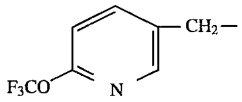 | H | " | " | " | |
| 439 | " | $CH_3$ | " | " | " | |
| 440 | 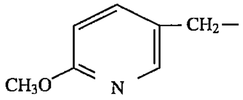 | H | $CH_3$ | CH | $NO_2$ | |
| 441 | " | $CH_3$ | " | " | " | |
| 442 | 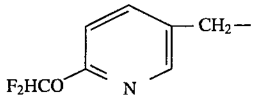 | H | " | " | " | |
| 443 | " | $CH_3$ | " | " | " | |

TABLE 1-continued
Structure Formula
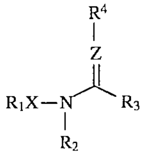
| Compound No. | $R_1X$ | $R_2$ | $R_3$ | Z | $R_4$ | Physical Properties [ ] m.p. °C. |
|---|---|---|---|---|---|---|
| 444 | 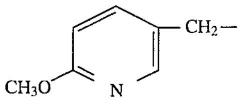 | H | " | " | " | |
| 445 | " | $CH_3$ | " | " | " | |
| 446 | 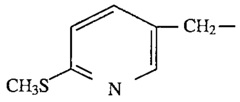 | H | " | " | " | |
| 447 | " | $CH_3$ | " | " | " | |
| 448 | 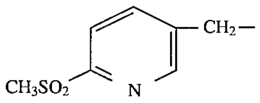 | H | " | " | " | |
| 449 | " | $CH_3$ | " | " | " | |
| 450 | 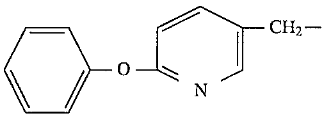 | H | " | " | " | |
| 451 | " | $CH_3$ | " | " | " | |
| 452 | 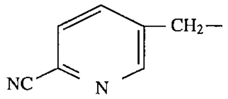 | H | $CH_3$ | CH | $NO_2$ | |
| 453 | " | $CH_3$ | " | " | " | |

TABLE 1-continued
Structure Formula
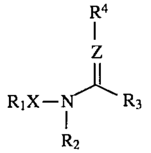
| Compound No. | $R_1X$ | $R_2$ | $R_3$ | Z | $R_4$ | Physical Properties [ ] m.p. °C. |
|---|---|---|---|---|---|---|
| 454 | 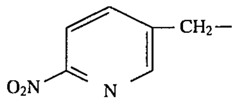 | H | " | " | " | |
| 455 | " | $CH_3$ | " | " | " | |
| 456 | 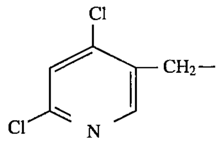 | H | " | " | " | |
| 457 | " | $CH_3$ | " | " | " | |
| 458 | 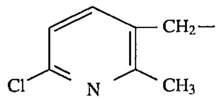 | H | " | " | " | |
| 459 | " | $CH_3$ | " | " | " | |
| 460 | 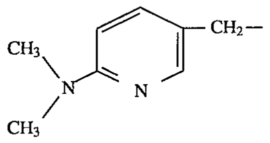 | H | " | " | " | |
| 461 | " | $CH_3$ | " | " | " | |
| 462 | 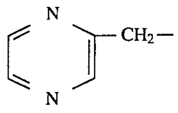 | H | $CH_3$ | CH | $NO_2$ | |
| 463 | " | $CH_3$ | " | " | " | |

TABLE 1-continued
Structure Formula
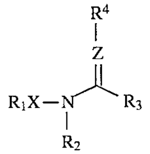
| Compound No. | $R_1X$ | $R_2$ | $R_3$ | Z | $R_4$ | Physical Properties [ ] m.p. °C. |
|---|---|---|---|---|---|---|
| 464 | 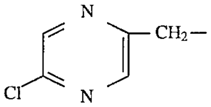 | H | " | " | " | |
| 465 | " | $CH_3$ | " | " | " | |
| 466 | 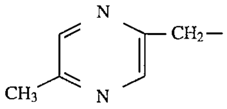 | H | " | " | " | |
| 467 | " | $CH_3$ | " | " | " | |
| 468 | 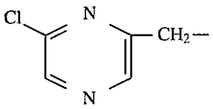 | H | " | " | " | |
| 469 | " | $CH_3$ | " | " | " | |
| 470 | 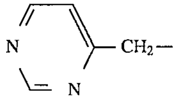 | H | " | " | " | |
| 471 | " | $CH_3$ | " | " | " | |
| 472 | 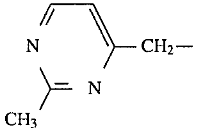 | H | " | " | " | |

TABLE 1-continued
Structure Formula
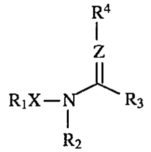
| Compound No. | $R_1X$ | $R_2$ | $R_3$ | Z | $R_4$ | Physical Properties [ ] m.p. °C. |
|---|---|---|---|---|---|---|
| 473 | 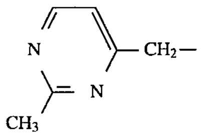 | $CH_3$ | $CH_3$ | CH | $NO_2$ | |
| 474 | 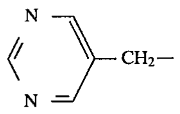 | H | " | " | " | |
| 475 | " | $CH_3$ | " | " | " | |
| 476 | 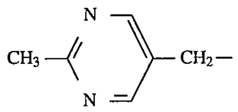 | H | " | " | " | |
| 477 | " | $CH_3$ | " | " | " | |
| 478 | 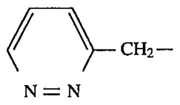 | H | " | " | " | |
| 479 | " | $CH_3$ | " | " | " | |
| 480 | 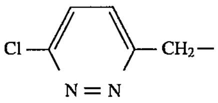 | H | " | " | " | |
| 481 | " | $CH_3$ | " | " | " | |
| 482 | 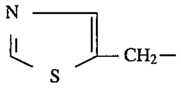 | H | " | " | " | |

TABLE 1-continued
Structure Formula
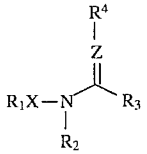
| Compound No. | $R_1X$ | $R_2$ | $R_3$ | Z | $R_4$ | Physical Properties [ ] m.p. °C. |
|---|---|---|---|---|---|---|
| 483 | " | $CH_3$ | " | " | " | |
| 484 | 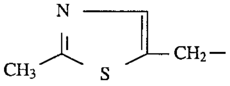 | H | $CH_3$ | CH | $NO_2$ | |
| 485 | " | $CH_3$ | " | " | " | |
| 486 | 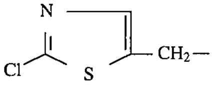 | H | " | " | " | |
| 487 | " | $CH_3$ | " | " | " | |
| 488 | " | " | $C_2H_5$ | " | " | |
| 489 | " | $C_2H_5$ | $CH_3$ | " | " | |
| 490 | 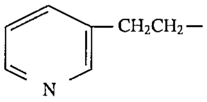 | H | " | " | " | |
| 491 | " | $CH_3$ | " | " | " | |
| 492 | 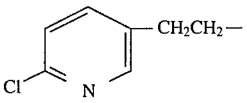 | H | " | " | " | |
| 493 | " | $CH_3$ | " | " | " | |
| 494 | 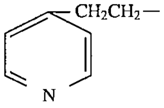 | H | " | " | " | |
| 495 | " | $CH_3$ | " | " | " | |

TABLE 1-continued
Structure Formula
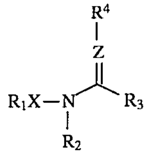
| Compound No. | $R_1X$ | $R_2$ | $R_3$ | Z | $R_4$ | Physical Properties [ ] m.p. °C. |
|---|---|---|---|---|---|---|
| 496 | 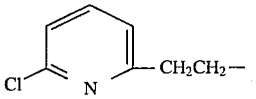 | H | $CH_3$ | CH | $NO_2$ | |
| 497 | " | $CH_3$ | " | " | " | |
| 498 | 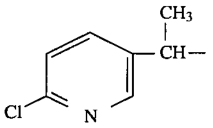 | H | " | " | " | |
| 499 | " | $CH_3$ | " | " | " | |
| 500 | 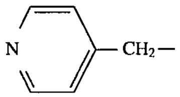 | H | " | " | " | |
| 501 | " | $CH_3$ | " | " | " | |
| 502 | 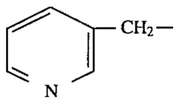 | H | H | CH | $NO_2$ | |
| 503 | " | " | $CH_3$ | " | " | |
| 504 | " | " | $CH_2Cl$ | " | " | |
| 505 | " | " | $C_2H_5$ | " | " | |
| 506 | " | " | $C_3H_7(i)$ | " | " | |
| 507 | " | " | $C_4H_9(t)$ | " | " | |
| 508 | " | $CH_3$ | H | " | " | |
| 509 | " | " | $CH_3$ | " | " | |
| 510 | " | " | $CH_2Cl$ | " | " | |
| 511 | " | " | $C_2H_5$ | " | " | |
| 512 | " | " | 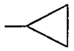 | " | " | |

TABLE 1-continued

Structure Formula

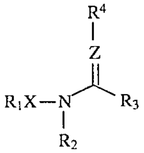

| Compound No. | $R_1X$ | $R_2$ | $R_3$ | Z | $R_4$ | Physical Properties [ ] m.p. °C. |
|---|---|---|---|---|---|---|
| 513 | 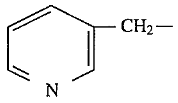 | $CH_3$ | $C_3H_7$(i) | CH | $NO_2$ | |
| 514 | " | " | $C_4H_9$(t) | " | " | |
| 515 | " | $C_2H_5$ | H | " | " | |
| 516 | " | " | $CH_3$ | " | " | |
| 517 | " | " | $C_2H_5$ | " | " | |
| 518 | " | 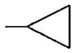 | H | " | " | |
| 519 | " | " | $CH_3$ | " | " | |
| 520 | " | " | $C_2H_5$ | " | " | |
| 521 | " | $COCH_3$ | H | " | " | |
| 522 | " | " | $CH_3$ | " | " | |
| 523 | " | " | $C_2H_5$ | " | " | |
| 524 | " | $SO_2CH_3$ | H | " | " | |
| 525 | " | " | $CH_3$ | " | " | |
| 526 | " | " | $C_2H_5$ | " | " | |
| 527 | 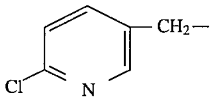 | H | H | CH | CN | |
| 528 | " | " | $CH_3$ | " | " | [95-98] |
| 529 | " | " | $CH_2Cl$ | " | " | |
| 530 | " | " | $C_2H_5$ | " | " | |
| 531 | " | " | $C_3H_7$(i) | " | " | |
| 532 | " | " | $C_4H_9$(t) | " | " | |
| 533 | " | " | $CH=CH_2$ | " | " | |
| 534 | " | " | $CH=CHCH_3$ | " | " | |
| 535 | " | " | $CH_2CN$ | " | " | |
| 536 | " | " | $CH_2NO_2$ | " | " | |
| 537 | " | " | $CH_2COOC_2H_5$ | " | " | |

TABLE 1-continued
Structure Formula
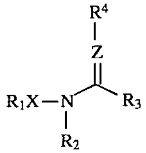
| Compound No. | $R_1X$ | $R_2$ | $R_3$ | Z | $R_4$ | Physical Properties [ ] m.p. °C. |
|---|---|---|---|---|---|---|
| 538 | 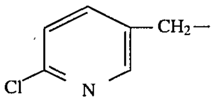 | H | 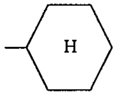 | CH | CN | |
| 539 | " | " | 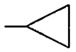 | " | " | |
| 540 | " | " | —$CH_2$— 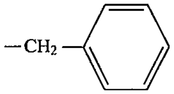 | " | " | |
| 541 | " | " | CH=CH— 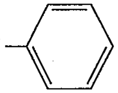 | " | " | |
| 542 | " | $CH_3$ | H | " | " | |
| 543 | " | " | $CH_3$ | " | " | $n_D^{29}$ 1.5941 |
| 544 | " | " | $CH_2Cl$ | " | " | |
| 545 | " | " | $C_2H_5$ | " | " | |
| 546 | " | " | $C_3H_7$(i) | " | " | |
| 547 | " | " | $C_4H_9$(t) | " | " | |
| 548 | " | " | $CH=CH_2$ | " | " | |
| 549 | " | " | $CH=CHCH_3$ | " | " | |
| 550 | 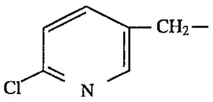 | $CH_3$ | $CH_2CN$ | CH | CN | |
| 551 | " | " | $CH_2NO_2$ | " | " | |
| 552 | " | " | $CH_2COOC_2H_5$ | " | " | |
| 553 | " | " | 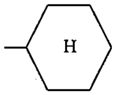 | " | " | |

TABLE 1-continued
Structure Formula
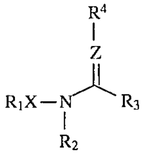
| Compound No. | $R_1X$ | $R_2$ | $R_3$ | Z | $R_4$ | Physical Properties [ ] m.p. °C. |
|---|---|---|---|---|---|---|
| 554 | " | " | 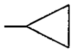 | " | " | |
| 555 | " | " | 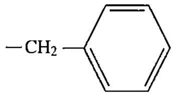 | " | " | |
| 556 | " | " | 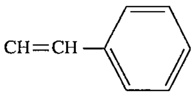 | " | " | |
| 557 | " | $C_2H_5$ | H | " | " | |
| 558 | " | " | $CH_3$ | " | " | |
| 559 | " | " | $C_2H_5$ | " | " | |
| 560 | " | $C_3H_7$(i) | H | " | " | |
| 561 | " | " | $CH_3$ | " | " | |
| 562 | 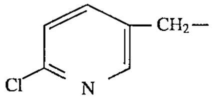 | $C_3H_7$(i) | $C_2H_5$ | CH | CN | |
| 563 | " | 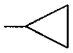 | H | " | " | |
| 564 | " | " | $CH_3$ | " | " | |
| 565 | " | " | $C_2H_5$ | " | " | |
| 566 | " | $CH_2CH=CH_2$ | H | " | " | |
| 567 | " | " | $CH_3$ | " | " | |
| 568 | " | " | $C_2H_5$ | " | " | |
| 569 | " | 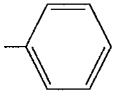 | H | " | " | |

TABLE 1-continued
Structure Formula
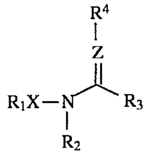
| Compound No. | $R_1X$ | $R_2$ | $R_3$ | Z | $R_4$ | Physical Properties [ ] m.p. °C. |
|---|---|---|---|---|---|---|
| 570 | " | " | $CH_3$ | " | " | |
| 571 | " | " | $C_2H_5$ | " | " | |
| 572 | " | CHO | H | " | " | |
| 573 | " | " | $CH_3$ | " | " | |
| 574 | 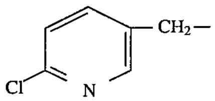 | CHO | $C_2H_5$ | CH | CN | |
| 575 | " | $COCH_3$ | H | " | " | |
| 576 | " | " | $CH_3$ | " | " | |
| 577 | " | " | $C_2H_5$ | " | " | |
| 578 | " | $SO_2CH_3$ | H | " | " | |
| 579 | " | " | $CH_3$ | " | " | |
| 580 | " | " | $C_2H_5$ | " | " | |
| 581 | " | $COOC_2H_5$ | H | " | " | |
| 582 | " | " | $CH_3$ | " | " | |
| 583 | " | " | $C_2H_5$ | " | " | |
| 584 | " | $OC_2H_5$ | H | " | " | |
| 585 | " | " | $CH_3$ | " | " | |
| 586 | " | " | $C_2H_5$ | " | " | |
| 587 | " | $CH_2C{=}CH$ | H | " | " | |
| 588 | " | " | $CH_3$ | " | " | |
| 589 | " | " | $C_2H_5$ | " | " | |
| 590 | 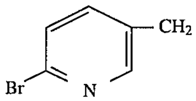 | H | $CH_3$ | CH | CN | |
| 591 | " | $CH_3$ | " | " | " | |
| 592 | 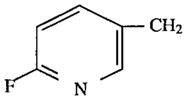 | H | " | " | " | |
| 593 | " | $CH_3$ | " | " | " | |

TABLE 1-continued
Structure Formula
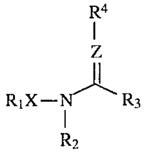
| Compound No. | R₁X | $R_2$ | $R_3$ | Z | $R_4$ | Physical Properties [ ] m.p. °C. |
|---|---|---|---|---|---|---|
| 594 | 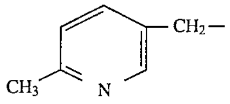 | H | " | " | " | |
| 595 | " | $CH_3$ | " | " | " | |
| 596 | 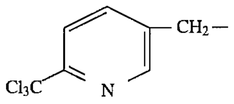 | H | " | " | " | |
| 597 | " | $CH_3$ | " | " | " | |
| 598 | 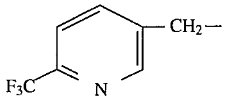 | H | " | " | " | |
| 599 | " | $CH_3$ | " | " | " | |
| 600 | 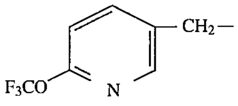 | H | " | " | " | |
| 601 | " | $CH_3$ | " | " | " | |
| 602 | 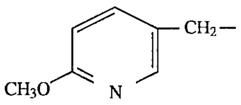 | H | $CH_3$ | CH | CN | |
| 603 | " | $CH_3$ | " | " | " | |

TABLE 1-continued
Structure Formula
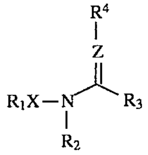
| Compound No. | $R_1X$ | $R_2$ | $R_3$ | Z | $R_4$ | Physical Properties [ ] m.p. °C. |
|---|---|---|---|---|---|---|
| 604 | 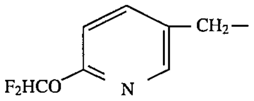 | H | " | " | " | |
| 605 | " | $CH_3$ | " | " | " | |
| 606 | 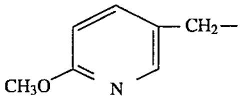 | H | " | " | " | |
| 607 | " | $CH_3$ | " | " | " | |
| 608 | 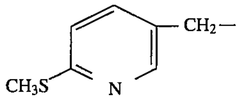 | H | " | " | " | |
| 609 | " | $CH_3$ | " | " | " | |
| 610 | 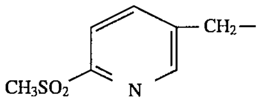 | H | " | " | " | |
| 611 | " | $CH_3$ | " | " | " | |
| 612 | 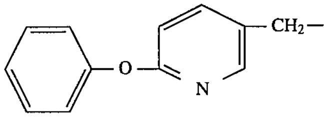 | H | " | " | " | |
| 613 | " | $CH_3$ | " | " | " | |

TABLE 1-continued
Structure Formula
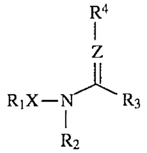
| Compound No. | $R_1X$ | $R_2$ | $R_3$ | Z | $R_4$ | Physical Properties [ ] m.p. °C. |
|---|---|---|---|---|---|---|
| 614 | 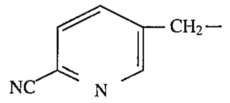 | H | $CH_3$ | CH | CN | |
| 615 | " | $CH_3$ | " | " | " | |
| 616 | 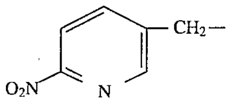 | H | " | " | " | |
| 617 | " | $CH_3$ | " | " | " | |
| 618 | 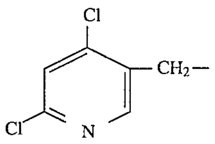 | H | " | " | " | |
| 619 | " | $CH_3$ | " | " | " | |
| 620 | 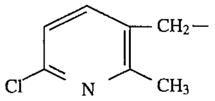 | H | " | " | " | |
| 621 | " | $CH_3$ | " | " | " | |
| 622 | 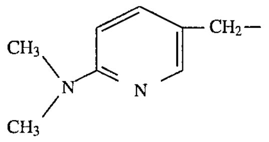 | H | " | " | " | |
| 623 | " | $CH_3$ | " | " | " | |

TABLE 1-continued
Structure Formula
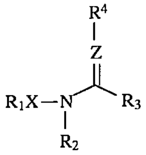
| Compound No. | $R_1X$ | $R_2$ | $R_3$ | Z | $R_4$ | Physical Properties [ ] m.p. °C. |
|---|---|---|---|---|---|---|
| 624 | 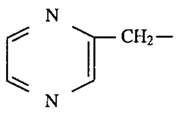 | H | $CH_3$ | CH | CN | |
| 625 | " | $CH_3$ | " | " | " | |
| 626 | 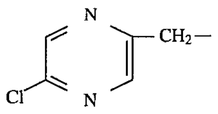 | H | " | " | " | |
| 627 | " | $CH_3$ | " | " | " | |
| 628 | 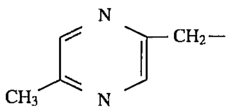 | H | " | " | " | |
| 629 | " | $CH_3$ | " | " | " | |
| 630 | 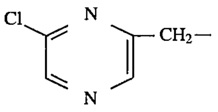 | H | " | " | " | |
| 631 | " | $CH_3$ | " | " | " | |
| 632 | 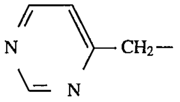 | H | " | " | " | |
| 633 | " | $CH_3$ | " | " | " | |

TABLE 1-continued
Structure Formula
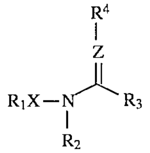
| Compound No. | $R_1X$ | $R_2$ | $R_3$ | Z | $R_4$ | Physical Properties [ ] m.p. °C. |
|---|---|---|---|---|---|---|
| 634 | 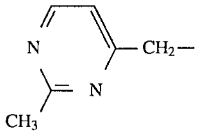 | H | " | " | " | |
| 635 | 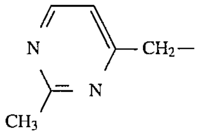 | $CH_3$ | $CH_3$ | CH | CN | |
| 636 | 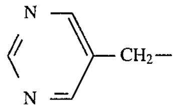 | H | " | " | " | |
| 637 | " | $CH_3$ | " | " | " | |
| 638 | 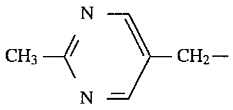 | H | " | " | " | |
| 639 | " | $CH_3$ | " | " | " | |
| 640 | 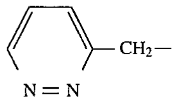 | H | " | " | " | |
| 641 | " | $CH_3$ | " | " | " | |

TABLE 1-continued
Structure Formula
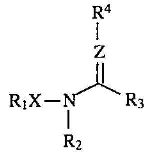
| Compound No. | $R_1X$ | $R_2$ | $R_3$ | Z | $R_4$ | Physical Properties [ ] m.p. °C. |
|---|---|---|---|---|---|---|
| 642 | 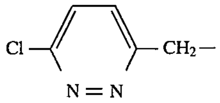 | H | " | " | " | |
| 643 | " | $CH_3$ | " | " | " | |
| 644 | 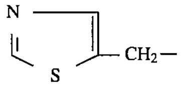 | H | $CH_3$ | CH | CN | |
| 645 | " | $CH_3$ | " | " | " | |
| 646 | 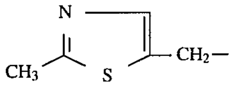 | H | " | " | " | |
| 647 | " | $CH_3$ | " | " | " | |
| 648 | 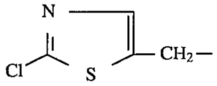 | H | " | " | " | |
| 649 | " | $CH_3$ | " | " | " | |
| 650 | " | " | $C_2H_5$ | " | " | |
| 651 | " | $C_2H_5$ | $CH_3$ | " | " | |
| 652 | 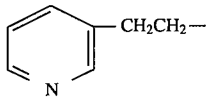 | H | $CH_3$ | CH | CN | |
| 653 | " | $CH_3$ | " | " | " | |

TABLE 1-continued
Structure Formula
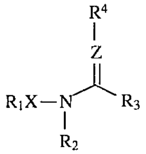
| Compound No. | $R_1X$ | $R_2$ | $R_3$ | Z | $R_4$ | Physical Properties [ ] m.p. °C. |
|---|---|---|---|---|---|---|
| 654 | 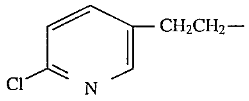 | H | " | " | " | |
| 655 | " | $CH_3$ | " | " | " | |
| 656 | 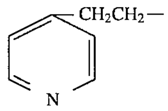 | H | " | " | " | |
| 657 | " | $CH_3$ | " | " | " | |
| 658 | 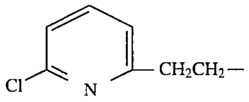 | H | " | " | " | |
| 659 | " | $CH_3$ | " | " | " | |
| 660 | 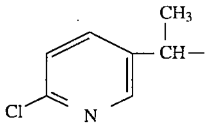 | H | " | " | " | |
| 661 | " | $CH_3$ | " | " | " | |
| 662 | 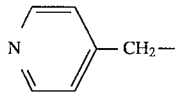 | H | " | " | " | |
| 663 | " | $CH_3$ | " | " | " | |

TABLE 1-continued
Structure Formula
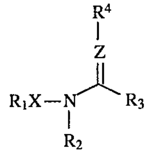
| Compound No. | $R_1X$ | $R_2$ | $R_3$ | Z | $R_4$ | Physical Properties [ ] m.p. °C. |
|---|---|---|---|---|---|---|
| 664 | 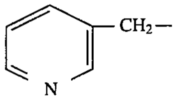 | H | H | CH | CN | |
| 665 | " | " | $CH_3$ | " | " | |
| 666 | " | " | $CH_2Cl$ | " | " | |
| 667 | " | " | $C_2H_5$ | " | " | |
| 668 | " | " | $C_3H_7(i)$ | " | " | |
| 669 | " | " | $C_4H_9(t)$ | " | " | |
| 670 | " | $CH_3$ | H | " | " | |
| 671 | " | " | $CH_3$ | " | " | |
| 672 | " | " | $CH_2Cl$ | " | " | |
| 673 | " | " | $C_2H_5$ | " | " | |
| 674 | " | " | 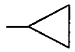 | " | " | |
| 675 | 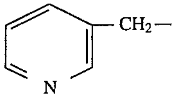 | $CH_3$ | $C_3H_7(i)$ | CH | CN | |
| 676 | " | " | $C_4H_9(t)$ | " | " | |
| 677 | " | $C_2H_5$ | H | " | " | |
| 678 | " | " | $CH_3$ | " | " | |
| 679 | " | " | $C_2H_5$ | " | " | |
| 680 | " | 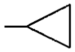 | H | " | " | |
| 681 | " | " | $CH_3$ | " | " | |
| 682 | " | " | $C_2H_5$ | " | " | |
| 683 | " | $COCH_3$ | H | " | " | |
| 684 | " | " | $CH_3$ | " | " | |
| 685 | " | " | $C_2H_5$ | " | " | |
| 686 | " | $SO_2CH_3$ | H | " | " | |

TABLE 1-continued
Structure Formula
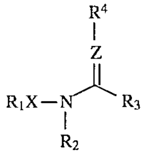
| Compound No. | $R_1X$ | $R_2$ | $R_3$ | Z | $R_4$ | Physical Properties [ ] m.p. °C. |
|---|---|---|---|---|---|---|
| 687 | 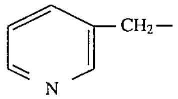 | $SO_2CH_3$ | $CH_3$ | CH | CN | |
| 688 | " | " | $C_2H_5$ | " | " | |
*1 $^1H$-NMR($CDCl_3$) δ; ppm 3.32 (s, 3H), 4.63 (s, 2H), 7.37 (d, 1H), 7.62 (dd, 1H), 8.37 (d, 1H)

The compounds of this invention exhibit high insecticidal activities against various species of insect pests such as cutworms, diamondback moth, aphids, leafhoppers and planthoppers. In recent years the decrease of the control effects of organophosphorus and carbamate insecticides, which is caused by the development of resistance to these insecticides, has become serious problem. In such situations, the development of new insecticides which is effective on the resistant pests has been desired. The compounds of this invention possess superior insecticidal activities against not only susceptible strains but also resistant ones.

The insecticides covered by this invention contain as active ingredients one or more types of the compounds as expressed by the general formula (1). These active ingredients, may be used as-produced but normally they are used in any of the forms which ordinary agricultural chemicals can take, namely wettable powder, dust, emulsifiable concentrate, suspension concentrates, smoking chemicals, fumigant, granule, or other formulations. For additives and carriers are used soybean flour, wheat flour or other vegetable flours, diatomaceous earth, apatite, gypsum, talc, pyrophyllite, clay or other fine mineral powders, when solid formulations are intended.

When liquid formulations are intended, then for solvents are used kerosene, mineral oil, petroleum, solvent naphtha, xylene, cyclohexane, cyclohexanone, dimethylformamide, dimethylsulfoxide, alcohol, acetone, water, etc. A surface active agent may, if necessary, be added in order to give a homogeneous and suitable formulation. The wettable powders, emulsifiable concentrates, suspension thus obtained are diluted with water concentrates, etc. into suspensions or emulsions of a prescribed concentration, before they are actually sprayed on plants in the field. In the case of dusts or granules, they are directly applied without further processing.

It goes without saying that the compound(s) of this invention is effective even alone, but it can be used by mixing with various types of insecticides, acaricides and fungicides.

Typical examples of acaricides and insecticides which can be used by mixing with the compounds of this invention are described below:

Acaricides (fungicides):

chlorobenzilate, chloropropylate, proclonol, bromopropylate, dicofol, dinobuton, binapacryl, chlordimeform, amitraz, propargite, PPPS, benzoximate, hexythiazox, fenbutatin oxide, polynactine, chinomethionat, thioquinox, chlorfenson, tetradifon, phenproxide, avermectins, clofentezine, flubenzimine, fenazaquin, pyridaben, fenproximate, chlorfenethol, thiophanate-methyl, benomyl, thiram, iprobenfos, edifenfos, fthalide, probenazole, isoprothiolane, chorothalonil, captan, polyoxin-B, blasticidin-S, kasugamycin, validamycin, tricyclazole, pyroquilon, phenazine oxide, mepronil, flutolanil, pencycuron, iprodione, hymexazole, metalaxyl, triflumizole, diclomezine, tecloftalam, vinclozolin, procymidone, bitertanol, triadimefon, prochloraz, pyrifenox, fenarimal, fenpropimorph, triforine, metalaxyl, oxycarboxin, pefrazoate, diclomedine, fluazinam, oxadixyl, ethoquinolac, TPTH, propamocarb, fosetyl, dihydrostreptomycin, anilazine, dithianon, diethofencarb.

Organophosphorus-type and carbamate-type insecticides (acaridides): fenthion, fenitrothion, diazinon, chlorpyrifos, oxydeprofos, vamidothion, phenthoate, dimethoate, formothion, malathion, trichlorfon, thiometon, phosmet, menazon, dichlorvos, acephate, EPBP, dialifos, parathion-methyl, oxydemeton-methyl, ethion, aldicarb, propoxur, methomyl, fenobucarb, BPMC, pyraclofos, monocrotophos, salithion, cartap, carbosulfan, carbofuran, benfuracarb, metolcarb, carbaryl, pirimicarb, ethiofencarb, fenoxycarb, Pyrethroide-type insecticides (acaricides): permethrin, cypermethrin, deltamethrin, fenvalerate, fenpropathrin, pyrethrins, allethrin, tetramethrin, resmethrin, parthrin, dimethrin, proparthrin, bifenthrin, prothrin, fluvalinate, cyhalothrin, cyhalothrin, flucythrinate, ethofenprox, cycloprothrin, tralomethrin, silaneophan.

Benzoylphenylurea-type and other types insecticides:

diflubenzuron, chlorfluazuron, triflumuron, teflubenzuron, buprofezin, pyriproxyfen, flufenoxuron, Machine oil.

Same examples of the formulations are given below. The carriers, surface-active agents, etc. that are added, however, are not limited to these Examples.

Example 7

Emulsifiable concentrate

| | |
|---|---|
| The compound of this invention | 10 parts |
| Alkylphenyl polyoxyethylene | 5 parts |
| Dimethyl formamide | 50 parts |
| Xylene | 35 parts |

These components are mixed and dissolved and, for use in spraying, the liquid mixture is water-diluted into an emulsion.

Example 8

Wettable powder

| | |
|---|---|
| The compound of this invention | 20 parts |
| Higher alcohol sulfuric ester | 5 parts |
| Diatomaceous earth | 70 parts |
| Silica | 5 parts |

These components are mixed and ground to fine powder, which for use in spraying, are water-diluted into a suspension.

Example 9

Dust

| | |
|---|---|
| The compound of this invention | 5 parts |
| Talc | 94.7 parts |
| Silica | 0.3 parts |

These are mixed and ground and used as-ground in spraying.

Example 10

Granule

| | |
|---|---|
| The compound of this invention | 5 parts |
| Clay | 73 parts |
| Bentonite | 20 parats |
| Sodium dioctylsulfosuccinate | 1 part |
| Sodium phosphate | 1 part |

The above compounds are granulated, and applied as it is when used.

Industrial applicability:

The tests below show the insecticidal activity of the compounds of this invention.

Test 1 Efficacy for cotton aphid 30 to 50 insects of cotton aphid per plot were inoculated using a small brush on cucumber leaves which were seeded in pots, 10 cm in diameter, and 10 days old after germination. A day later, wounded insect pests were removed, and a chemical solution, which was prepared in the way that the emulsifiable concentrate described in Example 7 of the above example of insecticide was diluted with water to 125 ppm of compound concentration according to the prescription, was sprayed. The pots were placed in a thermostatic room at temperature of 25 ° C. and humidity of 65%. The number of survival pests was counted 7 days later and the control efficacy was calculated by comparing with that of untreated plot. The results are shown in Table 2.

TABLE 2

| Compound No. | Control Efficacy (7 days later) 125 ppm |
|---|---|
| 1 | 100% |
| 2 | 100 |
| 3 | 100 |
| 4 | 100 |
| 6 | 100 |
| 8 | 100 |
| 10 | 100 |
| 16 | 100 |
| 20 | 100 |
| 21 | 100 |
| 22 | 100 |
| 23 | 100 |
| 24 | 100 |
| 25 | 100 |
| 27 | 100 |
| 29 | 100 |
| 31 | 100 |
| 32 | 100 |
| 33 | 100 |
| 38 | 100 |
| 44 | 100 |
| 48 | 100 |
| 50 | 100 |
| 51 | 100 |
| 53 | 100 |
| 57 | 100 |
| 60 | 100 |
| 62 | 100 |
| 64 | 100 |
| 66 | 100 |
| 68 | 100 |
| 70 | 100 |
| 72 | 100 |
| 73 | 100 |
| 74 | 100 |
| 78 | 100 |
| 80 | 100 |
| 82 | 100 |
| 84 | 100 |
| 86 | 100 |
| 88 | 100 |
| 92 | 100 |
| 96 | 100 |
| 100 | 100 |
| 102 | 100 |
| 115 | 100 |
| 116 | 100 |
| 120 | 100 |
| 124 | 100 |
| 130 | 100 |
| 132 | 100 |
| 136 | 100 |
| 144 | 100 |
| 145 | 100 |
| 146 | 100 |
| 148 | 100 |
| 149 | 100 |
| 150 | 100 |
| 151 | 100 |
| 152 | 100 |
| 163 | 100 |
| 164 | 100 |
| 169 | 100 |
| 170 | 100 |
| 171 | 100 |
| 172 | 100 |
| 173 | 100 |
| 174 | 100 |
| 177 | 100 |
| 178 | 100 |
| 188 | 100 |
| 189 | 100 |
| 190 | 100 |
| 194 | 100 |
| 203 | 100 |
| 206 | 100 |
| 213 | 100 |
| 236 | 100 |
| 366 | 100 |
| 368 | 100 |
| 381 | 100 |
| 383 | 100 |
| 543 | 100 |
| Comparative compound A | 27 |
| Comparative compound B | 100 |

Comparative compound A:

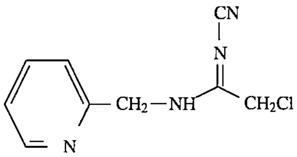

Comparative compound B:

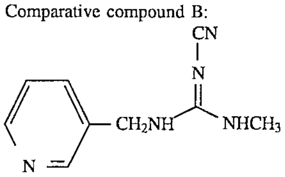

Test 2 Efficacy for green rice leafhopper

Rice seedlings of 7 days old after germination were immersed in a chemical solution, which was prepared in the way that the emulsifiable concentrate described in Example 7 of the above example of insecticide was diluted with water to 125 ppm of compound concentration according to prescription, for 30 seconds. After dried in air, the treated seedlings were placed in test tubes and 10 insects of 3rd-instar larvae of green rice leafhopper resistant to the organophosphorus and carbamate insecticides were inoculated. The tubes were covered with gauze, and placed in a thermostatic room at temperature of 25° C. and humidity of 65%. The mortality was checked 5 days later. The results are shown in Table 3.

TABLE 3

| Compound No. | % mortality (5 days later) 125 ppm |
|---|---|
| 1 | 100% |
| 2 | 100 |
| 4 | 100 |
| 6 | 100 |
| 8 | 100 |
| 10 | 100 |
| 16 | 100 |
| 18 | 100 |
| 20 | 100 |
| 21 | 100 |
| 22 | 100 |
| 23 | 100 |
| 24 | 100 |
| 25 | 100 |
| 27 | 100 |

TABLE 3-continued

| Compound No. | % mortality (5 days later) 125 ppm |
|---|---|
| 28 | 100 |
| 29 | 100 |
| 31 | 100 |
| 32 | 100 |
| 33 | 100 |
| 35 | 100 |
| 36 | 100 |
| 44 | 100 |
| 48 | 100 |
| 50 | 100 |
| 51 | 100 |
| 53 | 100 |
| 57 | 100 |
| 60 | 100 |
| 62 | 100 |
| 66 | 100 |
| 68 | 100 |
| 72 | 100 |
| 73 | 100 |
| 74 | 100 |
| 78 | 100 |
| 82 | 100 |
| 84 | 100 |
| 86 | 100 |
| 88 | 100 |
| 92 | 100 |
| 96 | 100 |
| 100 | 100 |
| 102 | 100 |
| 116 | 100 |
| 120 | 100 |
| 124 | 100 |
| 130 | 100 |
| 132 | 100 |
| 136 | 100 |
| 144 | 100 |
| 146 | 100 |
| 148 | 100 |
| 150 | 100 |
| 152 | 100 |
| 164 | 100 |
| 169 | 100 |
| 170 | 100 |
| 171 | 100 |
| 172 | 100 |
| 173 | 100 |
| 174 | 100 |
| 178 | 100 |
| 188 | 100 |
| 190 | 100 |
| 201 | 100 |
| 203 | 100 |
| 213 | 100 |
| 236 | 100 |
| 366 | 100 |
| 368 | 100 |
| 369 | 100 |
| 381 | 100 |
| Comparative Compound A | 0 |
| Comparative Compound B | 0 |
| Comparative Compound C | 0 |

Comparative compound A and B: The same as test 1

Compound C:

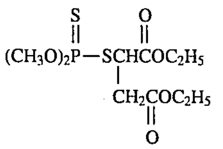

(malathion)

Test 3 Efficacy for rice armyworm

The test compounds were formulated into the wettable powder in the same manner as Example 8. The compounds were diluted with water to 125 ppm. A maize leaf was immersed in the chemical solution for 30 seconds. After air-dried, the treated leaf was placed in a petri dish and five 3rd-instar larvae of rice armyworm were inoculated. The petri dishes were covered with glass lids, and placed in a thermostatic room at 25° C. and 65% relative humidity. The mortality was checked 5 days later. Two replications were conducted in the each test. The results are shown in Table 4.

TABLE 4

| Compound No. | % mortality (5 days later) 125 ppm |
|---|---|
| 21 | 100% |
| 22 | 100 |
| 23 | 100 |
| 24 | 100 |
| 25 | 100 |
| 51 | 100 |
| 57 | 100 |
| 88 | 100 |
| 92 | 100 |
| 148 | 100 |
| 172 | 100 |
| 381 | 100 |
| Comparative compound A | 0 |
| Comparative compound B | 0 |
| Comparative compound D | 40 |

Comparative compound A and B: The same as Test 1

Compound D:

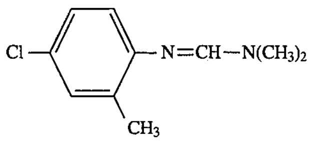

(chlordimeform)

We claim:

1. An insecticidal compound of the formula

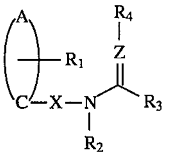

wherein

A completes a 6 membered aromatic ring having one heteroatomic ring member comprising nitrogen, provided, however, that the ring is not unsubstituted 2-pyridyl;

$R_1$ is hydrogen or $C_{1-5}$alkyl, $C_{1-5}$haloalkyl, $C_{1-5}$alkoxy, $C_{1-5}$alkylthio, $C_{1-5}$alkylsulfonyl, cyano, halogen, phenoxy, or $C_{1-5}$dialkylamino;

X is $C_{1-3}$alkylene or $C_{1-3}$alkylidene;

$R_2$ is hydrogen, carbamoyl, monoalkylcarbomoyl, $C_{1-5}$dialkylcarbamoyl, thiocarbamoyl, monoalkylthiocarbamoyl, sulfamoyl, monoalkylsulfamoyl, $C_{1-5}$dialkylsulfamoyl, $C_{1-5}$alkyl, $C_{1-5}$alkyl substituted with halogen, $C_{1-5}$alkoxy, $C_{1-5}$alkylthio, $C_{1-5}$alkoxycarbonyl, cyano, aryl, haloaryl, $C_{1-5}$alkoxyaryl, furyl, thienyl, pyridyl, halopyridyl, thiazolyl or halothiazolyl, $C_{2-5}$alkenyl, $C_{2-5}$alkynyl, $C_{3-8}$cycloalkyl, $C_{3-8}$cycloalkenyl, aryl, or the radical

—Y—$R_5$ wherein

Y is O, $S(O)_n$, CO, CS or $CO_2$;

n is O, 1 or 2, $R_5$ is hydrogen, $C_{1-5}$alkyl, $C_{2-5}$alkenyl, $C_{2-5}$alkynyl, $C_{3-8}$cycloalkyl, $C_{3-5}$cycloalkenyl, aryl or haloaryl;

$R_3$ is hydrogen, $C_{1-5}$alkyl, $C_{1-5}$alkyl substituted with halogen, $C_{1-5}$alkoxy, $C_{1-5}$alylthio, $C_{1-5}$alkoxycarbonyl, cyano, aryl, haloaryl, amino, monoalkylamino, $C_{1-5}$dialkylamino, cyanoimino, N-halopyridyl-$C_{1-5}$alkylamino, N-(halopyridyl-$C_{1-5}$alkyl)-$C_{1-5}$alkylamino, $C_{2-5}$alkenyl, $C_{2-5}$alkynyl, $C_{3-8}$cycloalkyl, or $C_{3-5}$cycloalkenyl;

$R_4$ is cyano or nitro;

Z is CH or N;

with the proviso that the insecticidal compound of such formula can not be a compound wherein;

$R_1$ is hydrogen or $C_{1-5}$alkyl, $C_{1-5}$haloalkyl, $C_{1-5}$alkoxy, $C_{1-5}$alkylthio, $C_{1-5}$alkylsulfonyl, cyano, halogen, or $C_{1-5}$dialkylamino;

X is $C_{1-3}$alkylene or $C_{1-3}$alkylidene;

$R_2$is hydrogen, carbamoyl, monoalkylcarbamoyl, $C_{1-5}$dialkylcarbamoyl, thiocarbamoyl, monoalkylthiocarbamoyl, sulfamoyl, monoalkylsulfamoyl, $C_{1-5}$dialkylsulfamoyl, $C_{1-5}$alkyl, $C_{2-5}$alkenyl, $C_{2-5}$alkynyl, $C_{3-8}$cycloalkyl, $C_{3-5}$cycloalkenyl, aryl, or the radical

—Y—$R_5$ wherein

Y is O, S(O)n, CO, CS or $CO_2$, n is O, 1 or 2, $R_5$ is hydrogen, $C_{1-5}$alkyl, $C_{2-5}$alkenyl, $C_{2-5}$alkynyl, $C_{3-5}$cycloalkyl, $C_{3-5}$cycloalkenyl, or aryl;

$R_3$ is hydrogen, $C_{1-5}$alkyl, $C_{2-5}$alkenyl, $C_{2-5}$alkynyl, $C_{3-8}$cycloalkyl, or $C_{3-8}$cycloalkenyl;

$R_4$ is cyano or nitro;

Z is CH or N; and an insecticidal acceptable salt thereof.

2. An insecticidal compound according to claim 1 wherein $R_2$ is hydrogen, monoalkylcarbamoyl, $C_{1-5}$dialkylcarbamoyl, $C_{1-5}$alkyl, $C_{1-5}$alkyl substituted with halogen, $C_{1-5}$alkoxy, $C_{1-5}$alkylthio, $C_{1-5}$alkoxycarbonyl, cyano, aryl, haloaryl, $C_{1-5}$alkoxyaryl, furyl, thienyl, pyridyl, halopyridyl, thiazolyl, halothiazolyl, $C_{2-5}$alkenyl, $C_{2-5}$alkynyl, $C_{3-8}$cycloalkyl, aryl, or the radical

—Y—$R_5$ wherein is O, CO, $CO_2$, or $SO_2$;

$R_2$ is $C_{1-5}$alkyl, aryl or haloaryl;

$R_3$is hydrogen, $C_{1-5}$alkyl, $C_{1-5}$alkyl substituted with halogen, $C_{1-5}$alkoxy, $C_{1-5}$alkylthio, $C_{1-5}$alkoxycarbonyl, cyano, aryl, haloaryl, amino, monoalkylamino, $C_{1-5}$dialkylamino, cyanoimino, N-halopyridyl-$C_{1-5}$alkylamino, N-(halopyridyl-$C_{1-5}$alkyl)-$C_{1-5}$alkylamino, or $C_{3-8}$cycloalkyl;

Z is CH or N;

and an insecticidal acceptable salt thereof.

3. An insecticidal compound according to claim 2 wherein Z is N.

4. A pyridine compound of the formula

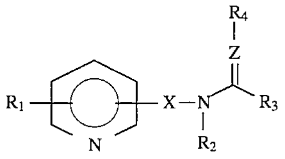

wherein $R_1$ represents hydrogen, $C_{1-5}$alkyl, $C_{1-5}$haloalkyl, $C_{1-5}$alkoxy, $C_{1-5}$alkylthio, $C_{1-5}$alkylsulfonyl, cyano, halogen, phenoxy or $C_{1-5}$dialkylamino;

X represents an optionally substituted $C_{1-3}$alkylene or $C_{1-3}$alkylidene;

$R_2$ represents hydrogen, carbamoyl, monoalkylcarbamoyl, $C_{1-5}$dialkylcarbamoyl, thiocarbamoyl, monoalkylthiocarbamoyl, sulfamoyl, monoalkylsulfamoyl, $C_{1-5}$dialkylsulfamoyl, $C_{1-5}$alkyl, $C_{2-5}$alkenyl, $C_{2-5}$alkynyl, $C_{3-8}$cycloalkyl, $C_{3-8}$cycloalkenyl, aryl, or the radical

—Y—$R_5$ wherein

Y represents O, CO, $CO_2$ or $SO_2$;

$R_5$ represents $C_{1-5}$alkyl, aryl, or haloaryl;

$R_3$ represents hydrogen, $C_{1-5}$alkyl, $C_{2-5}$alkenyl, $C_{2-5}$alkenyl, $C_{3-8}$cycloalkyl or $C_{3-8}$cycloalkenyl;

$R_4$ represents a cyano or a nitro;

Z represents CH or N;

and an insecticidal acceptable salt thereof.

5. A pyridine compound according to claim 4 wherein Z is N.

6. An insecticidal compound of the formula

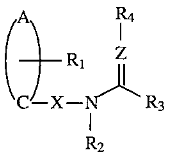

wherein

A completes a 6-membered aromatic ring selected from the group pyridyl, wherein pyridyl is substituted with $C_{1-5}$alkyl, $C_{1-5}$haloalkyl, $C_{1-5}$alkoxy, $C_{1-5}$alkylthio, $C_{1-5}$alkylsulfonyl, cyano, halogen, phenoxy or $C_{1-5}$dialkylamino, pyrazinyl, pyrazinyl substituted with halogen or thiazolyl substituted with halogen or $C_{1-5}$alkyl;

$R_1$is hydrogen or $C_{1-5}$alkyl, $C_{1-5}$haloalkyl, $C_{1-5}$alkoxy, $C_{1-5}$alkylthio, $C_{1-5}$alkylsulfonyl, cyano, halogen, phenoxy, or $C_{1-5}$dialkylamino;

X is $C_{1-3}$alkylene or $C_{1-3}$alkylidene;

$R_2$ is $C_{1-5}$alkyl substituted with halogen, $C_{1-5}$alkoxy, $C_{1-5}$alkylthio, $C_{1-5}$alkoxycarbonyl, cyano, aryl, haloaryl, $C_{1-5}$alkoxyaryl, furyl, thienyl, pyridyl, halopyridyl, thiazolyl or halothiazolyl;

$R_3$ is $C_{1-5}$alkyl substituted with halogen, $C_{1-5}$alkoxy, $C_{1-5}$alkylthio, $C_{1-5}$alkoxycarbonyl, cyano, aryl, haloaryl, amino, monoalkylamino, $C_{1-5}$dialkylamino, cyanomino, N-halopyridyl-$C_{1-5}$alkylamino or N-(halopyridyl-$C_{1-5}$alkyl)-$C_{1-5}$alkylamino;

$R_4$ is cyano or nitro;

Z is CH or N;

and an insecticidal acceptable salt thereof.

7. An insecticidal compound according to claim 6 wherein Z is N.

* * * * *